(12) United States Patent
Northrop et al.

(10) Patent No.: US 9,974,926 B2
(45) Date of Patent: May 22, 2018

(54) COATED TUBULAR SUPPORT MEMBERS AND METHODS OF MANUFACTURING SAME

(71) Applicants: STRYKER CORPORATION, Kalamazoo, MI (US); STRYKER EUROPEAN HOLDINGS I, LLC, Kalamazoo, MI (US)

(72) Inventors: Clay Northrop, Salt Lake City, UT (US); Ted Layman, Salt Lake City, UT (US); James Paul, Salt Lake City, UT (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 190 days.

(21) Appl. No.: 14/799,953

(22) Filed: Jul. 15, 2015

(65) Prior Publication Data

US 2016/0015928 A1 Jan. 21, 2016

Related U.S. Application Data

(60) Provisional application No. 62/026,544, filed on Jul. 18, 2014.

(51) Int. Cl.
*A61M 25/00* (2006.01)
*B29L 31/00* (2006.01)
(Continued)

(52) U.S. Cl.
CPC .... *A61M 25/0045* (2013.01); *A61M 25/0013* (2013.01); *A61M 25/0051* (2013.01);
(Continued)

(58) Field of Classification Search
CPC ....... B29C 59/021; B29C 63/18; B29C 63/48; B29C 63/481; B29C 69/007;
(Continued)

(56) References Cited

U.S. PATENT DOCUMENTS 5,106,455 A  4/1992 Jacobsen et al.
5,238,004 A  8/1993 Sahatjian et al.
(Continued)

FOREIGN PATENT DOCUMENTS

EP  0422887 A2  10/1990
EP  0920881 A2  6/1999
(Continued)

OTHER PUBLICATIONS

PCT International Search Report and Written Opinion for International Application No. PCT/US2015/040524, Applicant Stryker Corporation, forms PCT/ISA/210, 220, and 237, dated Mar. 18, 2016 (16 pages).
(Continued)

*Primary Examiner* — Jeffrey Wollschlager
(74) *Attorney, Agent, or Firm* — Vista IP Law Group LLP

(57) ABSTRACT

A tubular support member located in a distal portion of an elongate flexible medical device is provided with a plurality of wall openings, e.g., axially-spaced, substantially transverse slots, formed therein to thereby increase a flexibility of the support member. A layer of sealing material overlays an outer surface the support member so as to provide a sealed portion of the support member including the wall openings, the sealing material having respective flexible invaginations formed therein overlaying the wall openings in the support member so that the sealing material does not substantially impede flexibility of the support member.

8 Claims, 23 Drawing Sheets

(51) Int. Cl.
  *B29C 59/02* (2006.01)
  *B29C 63/48* (2006.01)
  *B29C 69/00* (2006.01)
  *B29C 63/18* (2006.01)
  *B29C 67/00* (2017.01)
  *B29C 33/50* (2006.01)
  *A61M 25/01* (2006.01)

(52) U.S. Cl.
  CPC ..... *A61M 25/0054* (2013.01); *A61M 25/0138* (2013.01); *B29C 33/50* (2013.01); *B29C 33/505* (2013.01); *B29C 59/021* (2013.01); *B29C 63/18* (2013.01); *B29C 63/48* (2013.01); *B29C 63/481* (2013.01); *B29C 67/004* (2013.01); *B29C 69/007* (2013.01); *B29C 69/008* (2013.01); *B29L 2031/753* (2013.01); *B29L 2031/7542* (2013.01)

(58) Field of Classification Search
  CPC .......... B29C 69/008; B29C 2793/0009; B29C 2793/0018; B29C 67/004; B29C 33/50; B29C 33/505; A61M 1/008; A61M 1/1008; A61M 3/2079; A61M 16/0418; A61M 16/0475; A61M 25/0045; A61M 25/0054; A61M 25/0013; A61M 25/0051; A61M 25/0138; A61M 25/0015; A61M 2025/0046; A61M 2025/0047; A61M 2025/0048; B29L 2031/7542; B29L 2031/753
  See application file for complete search history.

(56) References Cited

U.S. PATENT DOCUMENTS

| | | | |
|---|---|---|---|
| 5,357,979 A | 10/1994 | Imran | |
| 5,772,609 A | 6/1998 | Nguyen et al. | |
| 6,139,510 A | 10/2000 | Palermo | |
| 6,506,196 B1 | 1/2003 | Laufer | |
| 6,508,803 B1 | 1/2003 | Horikawa et al. | |
| 6,579,246 B2 | 6/2003 | Jacobsen et al. | |
| 6,766,720 B1 | 7/2004 | Jacobsen et al. | |
| 6,786,876 B2 | 9/2004 | Cox | |
| 6,918,882 B2 | 7/2005 | Skujins et al. | |
| 7,071,197 B2 | 7/2006 | Leonardi et al. | |
| 7,494,474 B2 | 2/2009 | Richardson et al. | |
| 7,494,687 B2 | 2/2009 | Cox | |
| 7,878,984 B2 | 2/2011 | Davis et al. | |
| 7,972,283 B2 | 7/2011 | Cornish et al. | |
| 7,989,042 B2 | 8/2011 | Obara et al. | |
| 8,409,169 B1 | 4/2013 | Moss | |
| 8,465,469 B2* | 6/2013 | Brightbill | A61M 25/0012 604/510 |
| 8,585,643 B2 | 11/2013 | Vo et al. | |
| 8,876,772 B2* | 11/2014 | Weber | A61L 29/041 604/164.01 |
| 2003/0069522 A1 | 4/2003 | Jacobsen et al. | |
| 2006/0074372 A1* | 4/2006 | Haga | A61M 25/0054 604/19 |
| 2007/0112331 A1* | 5/2007 | Weber | A61L 29/041 604/530 |
| 2008/0004568 A1* | 1/2008 | Jeffrey | A61M 25/0069 604/96.01 |
| 2010/0256606 A1 | 10/2010 | Lippert et al. | |
| 2013/0184644 A1 | 7/2013 | Vo et al. | |
| 2015/0119862 A1* | 4/2015 | Cajamarca | A61M 25/0045 604/530 |
| 2015/0297863 A1* | 10/2015 | Hannon | A61M 25/0009 604/544 |

FOREIGN PATENT DOCUMENTS

| | | |
|---|---|---|
| GB | 2319183 | 10/1997 |
| WO | 2014/077881 | 5/2014 |
| WO | 2014/077881 A1 | 5/2014 |

OTHER PUBLICATIONS

PCT Invitation to Pay Additional Fees for International Patent Application No. PCT/US2015/040524, Applicant Stryker Corporation, Form PCT/ISA/206, dated Nov. 6, 2015 (5 pages).

* cited by examiner

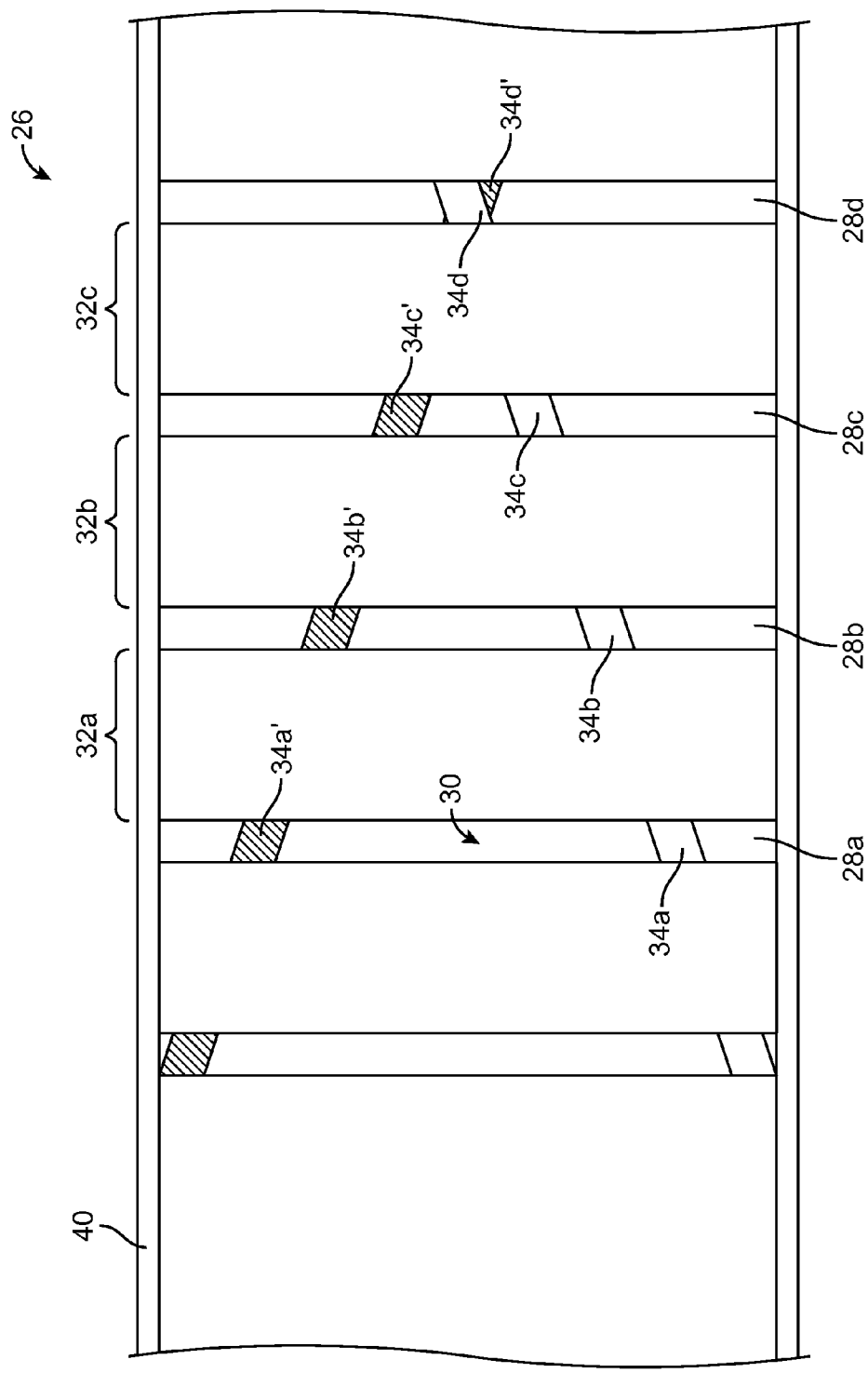

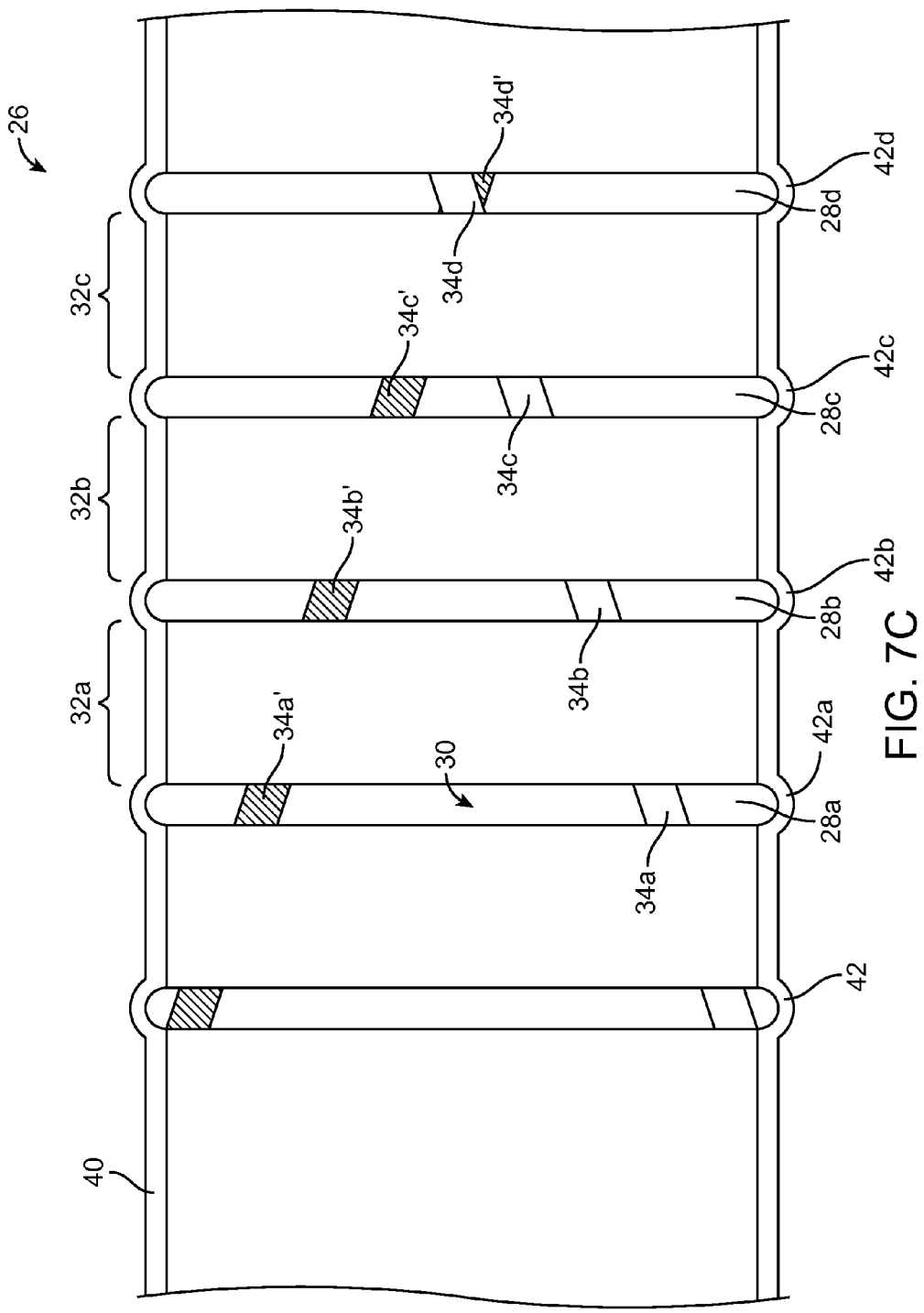

COATED TUBULAR SUPPORT MEMBERS AND METHODS OF MANUFACTURING SAME

RELATED APPLICATION DATA

The present application claims the benefit under 35 U.S.C. § 119 to U.S. provisional patent application Ser. No. 62/026,544, filed Jul. 18, 2014. The foregoing application is hereby incorporated by reference in its entirety.

FIELD

The disclosed inventions relate generally to medical devices, such as maneuverable catheters, guidewires and other elongate flexible members used to access target sites in a mammalian vasculature. More particularly, the disclosed inventions pertain to fluid sealed tubular support members used in such devices, and methods of their manufacture.

BACKGROUND

The use of intravascular catheters, guidewires and other types of elongate delivery members for accessing and treating various types of vascular disease is well-known. In general, a suitable intravascular catheter, guidewire, or other delivery member inserted into the vascular system, e.g., via introduction through a femoral or jugular artery or vein, and navigated through the vasculature to a desired target site. By using an appropriately sized device having the requisite performance characteristics, such as "pushability" "steerability", "torquability" and most important, distal tip flexibility, virtually any target site in the vascular system may be accessed, including within the tortuous cerebral vasculature.

For example, a stent for example, may be loaded in a reduced diameter configuration onto (or into) a catheter or other type of delivery wire, and then introduced into the lumen of a body vessel. Once delivered to a target location within the body vessel, the stent may then be expanded (or allowed to expand) to an enlarged configuration within the vessel to support and reinforce the vessel wall, while maintaining the vessel in an open, unobstructed condition. The stent may be configured to be self-expanding, expanded by an internal radial force such as a balloon, or a combination of self-expanding and balloon expandable.

By way of another example, balloon catheters are used in a number of endovascular applications, including for temporarily or permanently occluding blood flow either distal or proximal of a treatment site during neurological examinations, delivering diagnostic agents such as contrast media, assisting in neurovascular embolic coiling of an aneurysm or arteriovenous malformation (AVM), and dilating narrowed blood vessels caused by vasospasm. During therapeutic procedures such as the ones mentioned above, fast aspiration-mediated deflation of the balloon catheter is desired in order to quickly restore sufficient or normal blood flow to the brain in order to avoid potential neurological impairment. To facilitate rapid deflation, a single lumen balloon catheter may be provided with an internal axial support shaft made from a slotted, or otherwise perforated, tubular member, such as a metallic hypotube. Such slotted hypotubes provide superior performance characteristics (i.e., pushability, steerability, torquability, and flexibility) for accessing cerebral blood vessels. Exemplary slotted hypotubes manufactured for this purpose are disclosed and described in U.S. Pat. No. 8,585,643 and U.S. Patent Application Publication No. 2013/0184644, the entire disclosures of which are incorporated herein by reference, as though set forth in full. In particular, openings in the tubular support shaft underlying the balloon may function as inflation/deflation ports. However, openings in the tubular support shaft that are not enclosed by the balloon must be sealed (e.g., coated) to prevent egress of balloon inflation fluid delivered through the support shaft lumen. Such tubular support shafts may also be used, inter alia, as components of guidewires. When used as components of guidewires, the slotted hypotubes are preferably substantially sealed or prevent fluids from entering into the inner lumen of the tube, and also to enhance lubricity.

Methods of coating slotted support member hypotubes are described in U.S. Pat. No. 7,989,042, the entire disclosure of which is incorporated herein by reference, as though set forth in full. Such methods can either result in a substantially continuous coating, i.e., with most slots coated, or an at least partially discontinuous coating, i.e., with most slots open. However, the presence of coating materials within the slots reduces the flexibility and other performance characteristics of the hypotubes due to the stiffening caused by the coating material. This problem is exacerbated because the slotted hypotubes are often incorporated at the distal end portions of the respective catheters, guidewires and other delivery members, where having a high degree of flexibility is most crucial.

Accordingly, there is an ongoing need for providing adequately fluid sealed, slotted tubular support components for use in catheters, guidewires and other elongate delivery members used to access target sites in the vasculature, without compromising their performance characteristics.

SUMMARY

In accordance with one aspect of the disclosed inventions, an elongate flexible medical device comprises a support member comprising a tubular wall having a plurality of wall openings formed therein so as to increase a flexibility of the support member; and a layer of sealing material adjacent a surface of the support member so as to provide a sealed portion of the support member including the plurality of wall openings, the layer of sealing material comprising respective flexible invaginations formed therein adjacent respective wall openings in the tubular wall, so that the layer of sealing material does not substantially impede the flexibility of the tubular support member.

In one embodiment, the layer of sealing material is overlaying an outer surface of the support member so as to provide a sealed portion of the support member including the plurality of wall openings, the layer of sealing material comprising respective flexible invaginations formed therein overlaying respective wall openings in the tubular wall, so that the layer of sealing material does not substantially impede the flexibility of the tubular support member. By way of non-limiting examples, in one embodiment, the invaginations may extend radially inward into the respective wall openings in the support member. In another embodiment, the invaginations extend radially outward at locations overlaying the respective wall openings in the support member. In various embodiments, the wall openings formed in the support member comprise axially-spaced, substantially transverse slots, wherein the invaginations comprise respective portions of the sealing material layer that (i) extend radially inward into respective slots in the support member, or (2) extend radially outward at locations overlaying respective slots in the support member.

In accordance with another aspect of the disclosed inventions, a method of manufacturing an elongate flexible medical device includes the acts or steps of forming a plurality of openings in a wall of an elongate tubular support member to thereby increase a flexibility of the support member; forming a layer of sealing material on a surface of the support member so as to create a sealed portion of the support member including the plurality of wall openings; and forming a plurality of flexible invaginations in the layer of sealing material adjacent respective wall openings in the support member, such that the layer of sealing material does not substantially impede the flexibility of the support member.

In one such embodiment, the layer of sealing material is formed on an outer surface of the support member so as to create a sealed portion of the support member including the plurality of wall openings, wherein the plurality of invaginations in the layer of sealing material overlay respective wall openings in the support member, such that the layer of sealing material does not substantially impede the flexibility of the support member. In one embodiment, the invaginations in the sealing material layer extend into the wall openings of the support member. In another embodiment, the invaginations extend radially outward at locations overlaying the wall openings in the support member. In various embodiments, the wall openings formed in the support member comprise axially-spaced, substantially transverse slots.

In various embodiments, the layer of sealing material is formed by inserting a substrate into an axial lumen of the support member so that the substrate underlies and thereby blocks the respective wall openings; applying a coating of sealing material to the outer surface of the support member; and removing the substrate from the support member lumen. In one such embodiment, the substrate comprises a polymer (e.g., PTFE) beading having an outside diameter slightly greater than a diameter of the support member lumen, wherein the method further includes stretching the polymer beading to thereby neck down its outer diameter to a diameter slightly smaller than a diameter of the support member lumen, wherein inserting a substrate into the support member lumen comprises inserting the stretched polymer beading into the support member lumen; heating the polymer beading so that its outer diameter expands to approximately its pre-stretched diameter, thereby creating a tight fit of the polymer beading within the support member lumen, wherein the coating of sealing material is applied to the outer surface of the support member after expanding the outer diameter of the polymer beading so that sealing material is deposited directly on exposed portions of the polymer beading through the wall openings in the support member; and stretching and removing the polymer beading from the support member lumen, such that the sealing material remains intact and covers the wall openings in the support member. The invaginations may be formed in the sealing material by pressurizing the support member lumen after removing the polymer beading therefrom to thereby radially expand portions of the sealing material overlaying the respective wall openings. Alternatively, the invaginations may be formed in the sealing material by drawing a vacuum within the support member lumen after removing the polymer beading therefrom to thereby draw respective portions of the sealing material radially inward through the respective wall openings.

In another such embodiment, the substrate comprises a polymer (e.g., PTFE) tubing, and wherein the invaginations are formed in the sealing material by pressurizing an inner lumen of the polymer tubing after insertion into the support member lumen to cause portions of the polymer tubing to extend radially outward through respective wall openings in the support member, thereby forming bulges in portions of the sealing material overlaying the wall openings. The inner lumen of the polymer tubing may be pressurized prior to, or after applying the coating of sealing material to the outer surface of the support member.

In an alternative embodiment, the invaginations may be formed in the layer of sealing material by heating so as to soften the sealing material; and then drawing a vacuum within an inner axial lumen of the support member to thereby draw respective portions of the softened sealing material radially inward through the respective wall openings.

In accordance with further embodiments of the disclosed inventions, a method of manufacturing an elongate flexible medical device includes the steps or acts of forming a plurality of openings in a wall of an elongate tubular support member to thereby increase a flexibility of the support member; forming a layer of sealing material on an inner surface of the support member so as to create a sealed portion of the support member including the plurality of wall openings; and forming a plurality of invaginations in the layer of sealing material that underlie respective wall openings in the support member, such that the layer of sealing material does not substantially impede the flexibility of the support member.

In one such embodiment, the layer of sealing material is formed by inserting a polymer tubing into an axial lumen of the support member so that the polymer tubing underlies and thereby blocks the respective wall openings; heating so as to soften the polymer tubing after insertion into the support member lumen; and pressurizing an inner lumen of the softened polymer tubing relative to atmosphere exterior of the support member to cause portions of the polymer tubing to extend radially outward through respective wall openings in the support member, thereby forming bulges in portions of the polymer tubing underlying the wall openings. In another such embodiment, the layer of sealing material is formed by inserting a first polymer tubing into an axial lumen of the support member so that the polymer tubing underlies and thereby blocks the respective wall openings; inserting a second polymer tubing into an axial lumen of the first polymer tubing so that the second polymer tubing underlies the first polymer tubing; heating so as to soften the first and second polymer tubings; and pressurizing an inner lumen of the softened second polymer tubing relative to atmosphere exterior of the support member to cause portions of both the first polymer tubing and the second polymer tubing to extend radially outward through respective wall openings in the support member, thereby forming bulges in respective portions of the first and second polymer tubing underlying the wall openings. In still another such embodiment, the layer of sealing material is formed by inserting a polymer tubing into an axial lumen of the support member so that the polymer tubing underlies and thereby blocks the respective wall openings; gluing or fusing the polymer tubing to the interior surface of the support member; heating so as to soften the polymer tubing after insertion into the support member lumen; and drawing a vacuum within an inner axial lumen of the support member relative to atmosphere exterior of the support member to thereby draw respective portions of the softened sealing material adjacent respective wall openings radially inward. In yet another such embodiment, the layer of sealing material is formed by inserting the support member into an axial lumen of a substrate so that the substrate overlays and thereby blocks the respective wall openings; applying a coating of sealing material to the inner surface of the support member; and removing the substrate from the support member lumen.

Other and further aspects and features of embodiments will become apparent from the ensuing detailed description in view of the accompanying figures.

BRIEF DESCRIPTION OF THE DRAWINGS

FIG. 2A is a detailed perspective view of the balloon and balloon support shaft of the balloon catheter depicted in FIG. 2.

FIG. 2B is a detailed perspective view of three balloon support shafts according to various embodiments of the invention.

FIG. 2C is a detailed perspective view of the reinforced catheter shaft of the balloon catheter depicted in FIG. 2.

FIG. 7A is a detailed side view of a prior art balloon support shaft.

FIGS. 7B-7E are detailed side views of balloon support shafts constructed according to various embodiments of the disclosed inventions.

DETAILED DESCRIPTION OF THE ILLUSTRATED EMBODIMENTS

Figure 1:
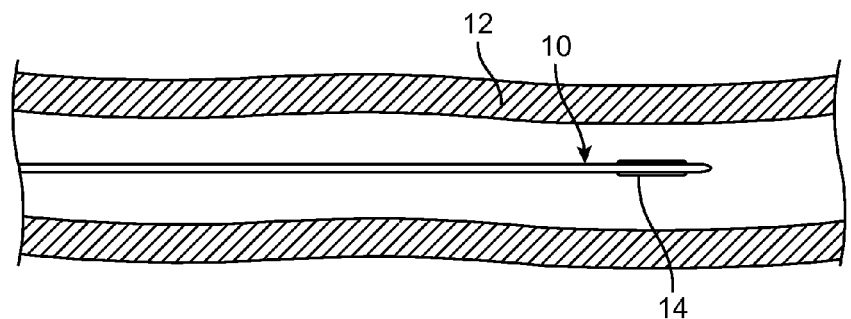
FIG. 1 is a plan view of a balloon catheter constructed according to one embodiment and disposed in a vessel.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 is a plan view of a balloon catheter 10 disposed in a body lumen 12, e.g., a blood vessel. Balloon catheter 10 includes a balloon 14 configured to expand in a body lumen, e.g., to the seal lumen 12. Balloon catheter 10 may also be used for other intravascular procedures. For example, balloon catheter 10 may be used in conjunction with other medical devices, such as a stent or a vaso-occlusive device, to treat and/or diagnose a medical condition.

Figure 2:
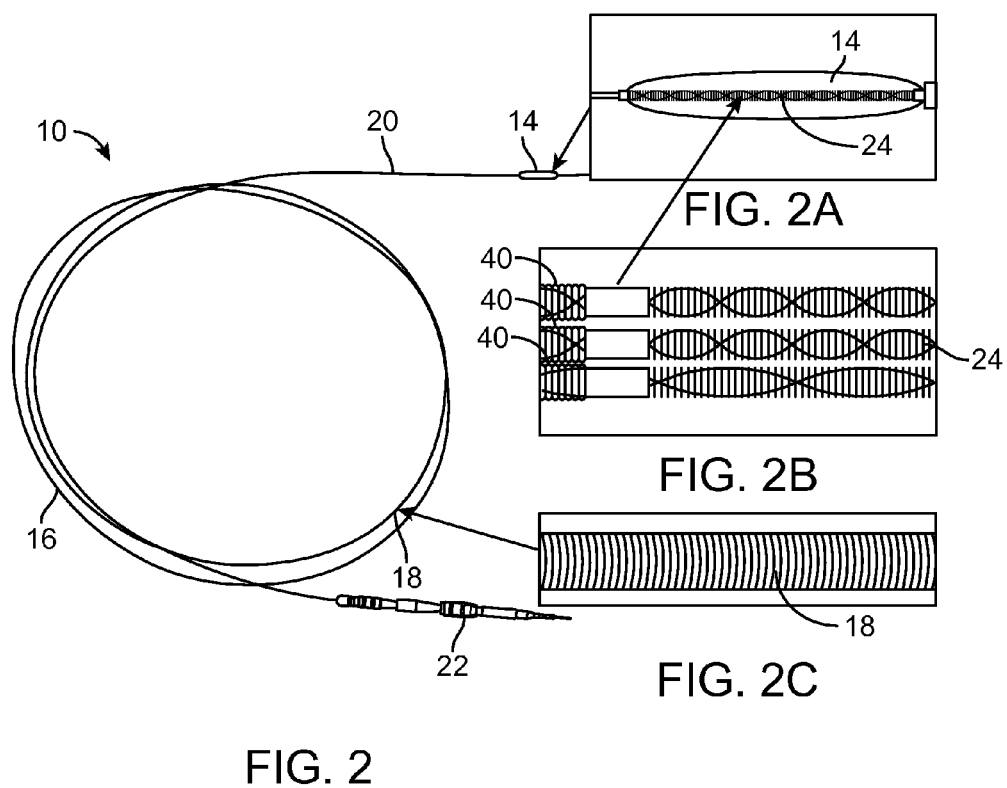
FIG. 2 is a perspective view of a balloon catheter constructed according to one embodiment, including insets showing the catheter shaft, the balloon and various balloon support shafts.

FIG. 2 shows a balloon catheter 10 including an elongate member 16 having a proximal portion 18 and a distal portion 20. In FIG. 2, much of the proximal portion 18 is wound into a loop to display the entire catheter shaft design. An inflation source 22, such as a 1 cc or 3 cc syringe 22, is attached to the elongate member 16 at its proximal end using a three-way stopcock. A balloon 14 is attached to the distal end of the elongate member 16. The balloon 14 is also shown in an inset (FIG. 2A) in sufficient detail to display the balloon support shaft 24 in the distal portion 20 of the elongate member 16. A second inset (FIG. 2B) shows several balloon support shafts 24 according to various embodiments. A third inset (FIG. 2C) shows a reinforced catheter shaft in the proximal portion 18 of the elongate member 16. As shown in FIG. 2B, the proximal (left) portion of the balloon support shaft 24, which is not configured to underlie the balloon 14, is coated with polymer coating/layer 40 to seal the openings/slots 28 formed therein (described below).

Figure 3A:
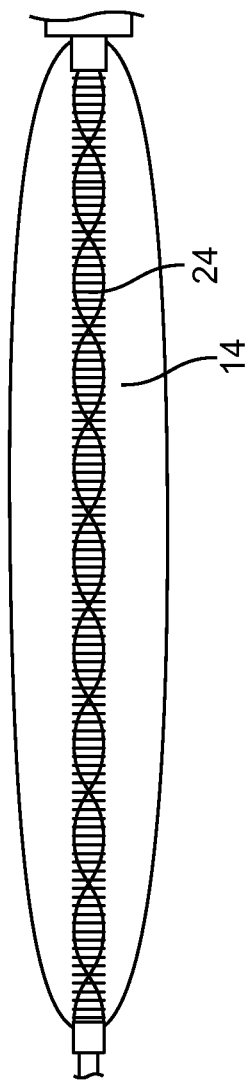
FIG. 3A is a detailed perspective view of a balloon catheter according to one embodiments.
Figure 3B:
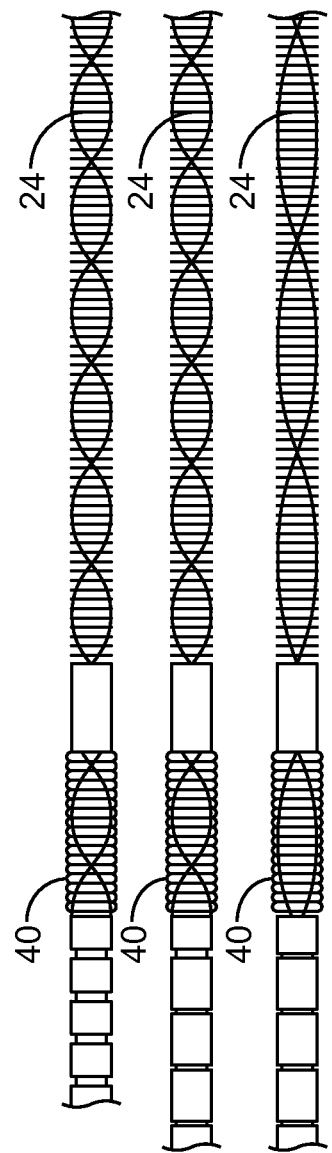
FIG. 3B is a detailed perspective view of various balloon support shafts according to various embodiments.

FIGS. 3A-6, 7B, 7C and 8 show various features of the balloon support shaft 24 according to various embodiments that will be discussed in greater detail below. As shown in FIGS. 3B, 4, 5, 7B and 7C, the balloon support shaft 24 has a tubular member 26 with openings, in the form of axially-spaced, substantially transverse slots 28, formed therein. When supporting a balloon 14 in a balloon catheter 10, as shown in FIG. 3A, at least a part of the tubular member 26 is disposed inside the balloon 14. The portion of the tubular member 26, which is not configured to underlie the balloon 14, is coated with polymer layer 40 to seal the slots formed therein (described below). The tubular member 26 defines a lumen 30 that accommodates a guidewire (not shown) and provides a fluid path for inflation and deflation of the balloon 14. The structure of the tubular member 26 allows fluid communication between the lumen 30 of the tubular member 26 and the interior of the balloon 14 through the slots 28. A guidewire seal (not shown) is provided at the distal end of the balloon 14 to provide a fluid seal about the guidewire.

An inflation source 22 is fluidly connected to the lumen 30 of the tubular member 26 into which it can introduce and withdraw inflation fluid and contrast medium. From the proximal opening of the lumen 30, the introduced fluid travels through lumen 30 of the tubular member 26 and around the guidewire disposed therein. In the portion of the tubular member 26 that does not underlie the balloon 14, the fluid is retained in the lumen 30 by the polymer layer 40 sealing the slots 28 in the tubular member 26. When the fluid reaches the portion of the tubular member 26 underlying the balloon 14, the fluid travels through the slots 28, and into the interior of the balloon 14 to facilitate inflation thereof. The balloon 14 can be deflated using the process in reverse.

Figure 7B:
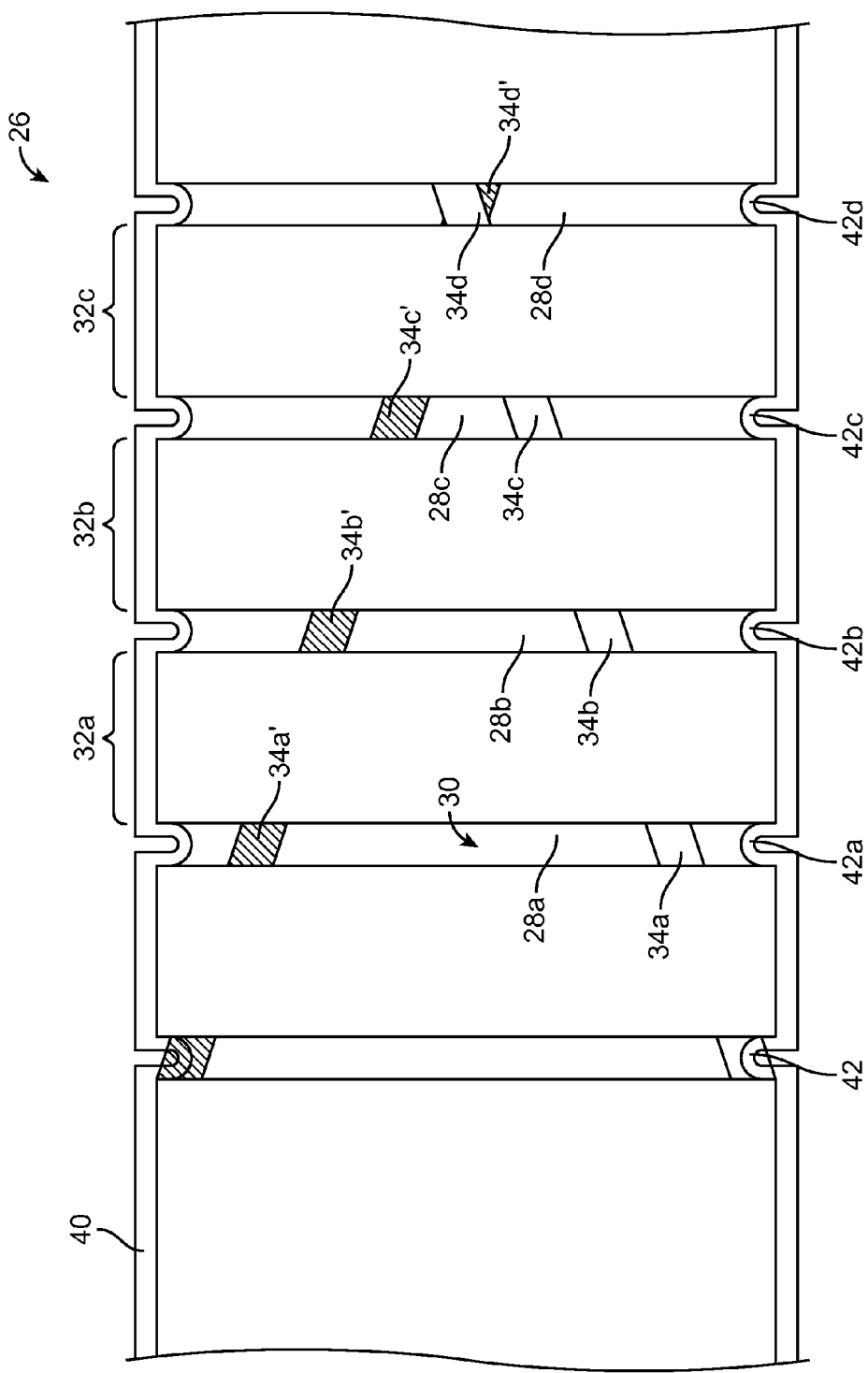

FIGS. 7B and 7C show the detailed structure of a tubular member 26 according to two embodiments. The tubular member 26 is generally a stack of annular segments 32. Tubular member 26 includes a plurality of slots 28 formed therein. Various embodiments of arrangements and configurations of slots 28 are contemplated. In some embodiments, at least some, if not all of slots 28 are disposed at the same or a similar angle with respect to the longitudinal axis of tubular member 26. As shown, slots 28 can be disposed at an angle that is perpendicular, or substantially perpendicular, and/or can be characterized as being disposed in a plane that is normal to the longitudinal axis of tubular member 26. However, in other embodiments, slots 28 can be disposed at an angle that is not perpendicular, and/or can be characterized as being disposed in a plane that is not normal to the longitudinal axis of tubular member 26. Additionally, a group of one or more slots 28 may be disposed at different angles relative to another group of one or more slots 28. The distribution and/or configuration of slots 30 can also include, to the extent applicable, any of those disclosed in U.S. Pat. No. 7,878,984, the entire disclosure of which is incorporated herein by reference, as though set forth in full.

Slots 28 enhance the flexibility of tubular member 26 while retaining suitable torque transmission characteristics. Slots 28 are formed such that the annular segments 32 are interconnected by one or more beams 34, i.e., the portion of tubular member 26 remaining after slots 28 are formed therein. Such an interconnected structure displays a relatively high degree of torsional stiffness, while retaining a desired level of lateral flexibility. In some embodiments, some adjacent slots 28 can be formed such that they include portions that overlap with each other about the circumference of tubular member 26. In other embodiments, some adjacent slots 28 can be disposed such that they do not necessarily overlap with each other, but are disposed in a pattern that provides the desired degree of lateral flexibility.

Additionally, slots 28 can be arranged along the length of, or about the circumference of, tubular member 26 to achieve desired properties. For example, adjacent slots 28, or groups of slots 28, can be arranged in a symmetrical pattern, such as being disposed essentially equally on opposite sides about the circumference of tubular member 26, or can be rotated by an angle relative to each other about the axis of tubular member 26. Further, adjacent slots 28, or groups of slots 28, may be equally spaced along the length of tubular member 26, or can be arranged in an increasing or decreasing density pattern, or can be arranged in a non-symmetric or irregular pattern. Other characteristics, such as slot size, slot shape and/or slot angle with respect to the longitudinal axis of tubular member 26, can also be varied along the length of tubular member 26 in order to vary the flexibility or other properties. In other embodiments, moreover, it is contemplated that the portions of the tubular member may not include any such slots 28.

As suggested above, slots 28 may be formed in groups of two, three, four, five, or more slots 28, which may be located at substantially the same location along the axis of tubular member 26. Alternatively, a single slot 28 may be disposed at some or all of these locations. Within the groups of slots 28, there may be included slots 28 that are equal in size (i.e., span the same circumferential distance around tubular member 26). In some of these as well as other embodiments, at least some slots 28 in a group are unequal in size (i.e., span a different circumferential distance around tubular member 26). Longitudinally adjacent groups of slots 28 may have the same or different configurations.

For example, some embodiments of tubular member 26 include slots 28 that are equal in size in a first group and then unequally sized in an adjacent group. It can be appreciated that in groups that have two slots 28 that are equal in size and are symmetrically disposed around the tube circumference, the centroid of the pair of beams 34 is coincident with the central axis of tubular member 26. Conversely, in groups that have two slots 28 that are unequal in size and whose beams 34 are directly opposed on the tube circumference, the centroid of the pair of beams 34 is offset from the central axis of tubular member 26. Some embodiments of tubular member 26 include only slot groups with centroids that are coincident with the central axis of the tubular member 26, only slot groups with centroids that are offset from the central axis of tubular member 26, or slot groups with centroids that are coincident with the central axis of tubular member 26 in a first group and offset from the central axis of tubular member 26 in another group. The amount of offset may vary depending on the depth (or length) of slots 28 and can include essentially any suitable distance.

Slots 28 can be formed by methods such as micromachining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 26 is formed by cutting and/or removing portions of the tube to form slots 28. Some example embodiments of appropriate micromachining methods and other cutting methods, and structures for tubular members including slots and medical devices including tubular members are disclosed in U.S. Pat. Publication No. 2003/0069522; and U.S. Pat. Nos. 7,878,984, 6,766,720 and 6,579,246, the entire disclosures of which are incorporated herein by reference, as though set forth in full. Some example embodiments of etching processes are described in U.S. Pat. No. 5,106,455, the entire disclosure of which is incorporated herein by reference, as though set forth in full. It should be noted that the methods for manufacturing balloon catheter 10 may include forming slots 28 in tubular member 26 using any of these or other manufacturing steps.

In at least some embodiments, slots 28 may be formed in tubular member using a laser cutting process. The laser cutting process may include essentially any suitable laser and/or laser cutting apparatus. For example, the laser cutting process may utilize a fiber laser. Utilizing processes like laser cutting may be desirable for a number of reasons. For example, laser cutting processes may allow tubular member 26 to be cut into a number of different cutting patterns in a precisely controlled manner. This may include variations in the slot width (which also may be termed "kerf"), annular segment width, beam height and/or width, etc. Furthermore, changes to the cutting pattern can be made without the need to replace the cutting instrument (e.g., a blade). This may also allow smaller tubes (e.g., having a smaller outer diameter) to be used to form tubular member 26 without being limited by a minimum cutting blade size. Consequently, tubular members 20 may be fabricated for use in neurological devices or other devices where a small size may be desired.

Because of the precision and control that may be achieved by cutting slots 28 with a laser, numerous additional variation can be achieved in slot 28 configurations, arrangements, etc. Still referring to FIGS. 7B and 7C, side views of tubular members 26 are illustrated. Tubular member 26 includes a plurality of annular segments 32 including annular segment 32a, annular segment 32b, and annular segment 32c. In this example, segment 32a is disposed longitudinally-adjacent (i.e., right next to) segment 32b and segment 32c is disposed longitudinally-adjacent segment 32b (oppositely segment 32a). The number of annular segments 32 in a given tubular member 26 may vary depending on the structure of tubular member 26. For example, as the number of slots 28 increases, the number of annular segments 32 may similarly increase. The invention is not intended to be limited to any particular number or arrangement of annular segments 32 for any given tubular member 26 or device including a tubular member 26.

Segments 32a/32b/32c can be understood to be generally circumferential or "round" portions of tubular member 26 that are defined between groups or sets of slots 28. For example, segment 32a is defined between a first group of slots 28a and a second group of slots 28b. Likewise, segment 32b is defined between group 28b and a third group of slots 28c. Moreover, segment 32c is defined between group 28c and a fourth group of slots 28d. In this example, each group 28a/28b/28c/28d includes two slots 28. However, any suitable number of slots 28 may be utilized for any group 28a/28b/28c/28d. Just like the annular segments 32, the invention is not intended to be limited to any number of slots 28, groups of slots 28, or number of slots 28 per group for any given tubular member 26 or device including a tubular member 26 with slots 28.

When slots 28 are formed in tubular member 26, a portion of tubular member 26 remains at the longitudinal location where slots 28 are formed and extends between longitudinally-adjacent annular segments 32. This portion is called a "beam" 34. Several beams 34 are illustrated in FIGS. 7B and 7C including beam 34a, beam 34a', beam 34b, beam 34b', beam 34c, beam 34c', beam 34d, and beam 34d'. Beams 34a/34a'/34b/34b'/34c/34c'/34d/34d' can be understood to be portions of tubular member 26 that connects or attaches longitudinally-adjacent annular segments 32. Each pair of longitudinally-adjacent annular segments (e.g., 32a and 32b) is attached by two beams (e.g., 34b and 34b'), which form a beam pair at the same longitudinal location along tubular member 26. Similarly, segment 32b is attached to segment 32c by beams 34c and 34c'. In this example, each group 28a/28b/28c/28d of slots 28 defines or leaves behind two, corresponding beams at a given longitudinal location. In FIGS. 7B and 7C, which illustrate tubular members 26 from the side, one beam (e.g., 34a, 34b, 34c, 34d) of each beam pair can be seen from the front and the other beam (e.g., 34a', 34b', 34c', 34d') of the beam pair can be seen from the back and is shaded for clarity.

Figure 8:
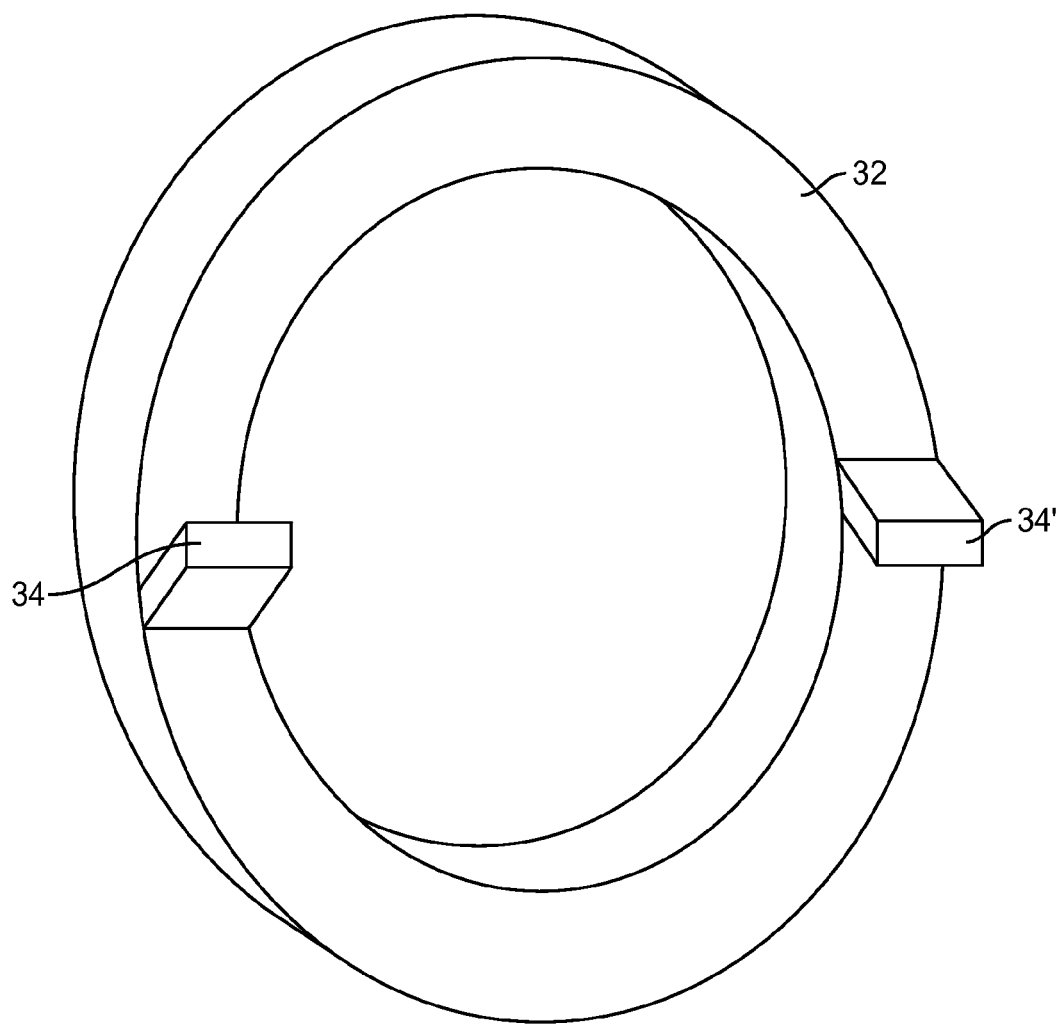
FIG. 8 is a detailed end view of an annular segment and two beams of a balloon support shaft constructed according to one embodiment.

The beams 34, 34' are formed in the tubular member 26 such that they meet the annular segments 32 at an oblique angle, as shown in FIG. 8. Further, each beam pair is formed in the tubular member 26 such that it is rotated about the longitudinal axis of the tubular member 26 from the previous beam pair. In this embodiment, each beam pair is angularly displaced or rotated by about eight degrees from the previous beam pair, resulting in a full rotation about every 45 beam pairs. The beam pairs form a double helix structure along the length of the tubular member 26 because of the oblique angle between beams 34 and annular segments 32, and the angular displacement between beam pairs. These helices, which rotate in the same direction, are shown in FIGS. 2, 3, 5, and 6.

As the angle of rotation between adjacent beams 34 is reduced, the portion of the annular segment 32 between beams 34 shortens until it is non-existent on one side and completely isolated from loading (bending, tension and compression) on the other side. In embodiments having small angles of rotation, such as the one depicted in FIG. 5, the beams 34 for a continuous helix. When such a structure is placed in compression or tension the helical line of beam pairs act as a continuous pair of fibers that effectively prevent length change of the structure. When loaded in tension the fibers are prevented from collapsing inward and straightening by the rib support of the annular segments 32. Conversely, when loaded in compression, the fibers are prevented from buckling individually outward by the annular segments 32.

Figure 6:
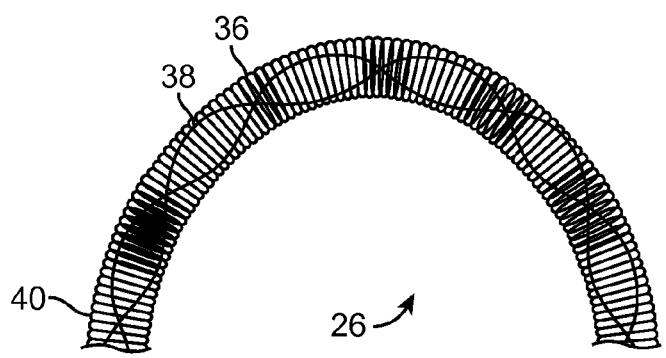
FIG. 6 is a perspective view of the balloon support shaft of FIG. 5 in a bent configuration.

As shown in FIG. 6, the double helix arrangement of beams 34 causes the tubular member 26 to bend in a segmented manner, with more bending occurring in the first region 36 where the beam pair in the helix defines an axis approximately parallel to the plane of bending. Almost no bending in the second region 38 where the beam pair axis is perpendicular to the plane of bending. Increasing the pitch of the helices increases the likelihood that several bending regions 36 will exist in the tightest predicted radius of curvature of the balloon catheter 10. As the angle of rotation between adjacent pairs of beams is increased the helix angle becomes tighter and the tubular member 26 may begin to twist into a ring when bent. The helix angle may be optimized to maximize both axial stiffness and isotropic properties in bending.

Figure 9:
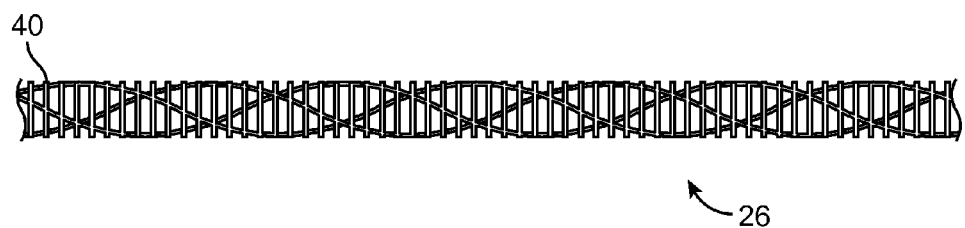
FIG. 9 is a perspective view of a balloon support shaft constructed according to one embodiment.

Increasing the number of beams 34 connecting each pair of annular segments 32 results in a tubular member 26 with more isotropic bending. Increasing the number connecting beams 34 from two to three gives the structure a more frequently repeating symmetry along its length. For example, a two beam structure (FIGS. 2, 3, 5, and 6) is symmetric at every 180 degrees of rotation while a three beam structure (FIGS. 9 and 10) is symmetric at every 120 degrees of rotation. The three beam structure will not be as soft as a two beam structure, and may be more useful in proximal regions of the balloon catheter where greater stiffness is desired.

Figure 13A:
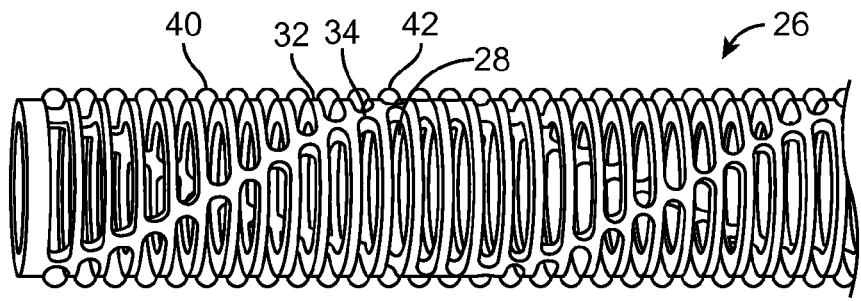
Figure 13B:
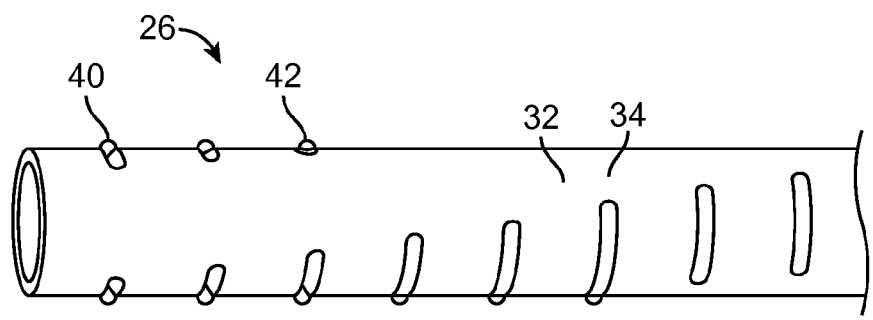
Figure 13C:
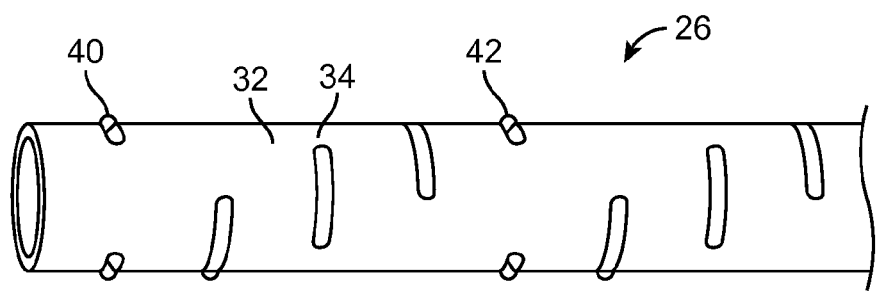

In a typical transvascular device, such as a balloon catheter 10, the proximal region of the device is typically in less tortuous anatomy and the bending stiffness is higher to allow the device to be pushed without bowing or buckling. Accordingly, it is desirable to create a microfabricated structure with stiffness that varies along the length of the device. For instance, the stiffness can decrease and/or increase along the length of the device. The stiffness can also decrease then increase and/or increase then decrease. The stiffness of the structure can be adjusted by increasing the beam 34 and/or annular segment 32 dimensions. These are typically varied at the same time in order to create a structure that has a more uniform distribution of stress. However when the width of the annular segment 32 dimension is increased the pitch of the helix is reduced, so that there are fewer bending regions per length, as shown in FIGS. 13A and 13B. To offset this effect, the rotational angle between beam 34 sets (two, three, or more beams) can be varied proportional to annular segment 32 width to maintain a relatively constant helical pitch along the length of the device. Compare FIGS. 13A and 13B. It can be seen in FIGS. 13A to 13C that as the annular segment 32 width increases the rotational angle can be increased without creating ring structures that will be loaded in bending, tension, or compression. This results in a device with higher bending stiffness and improved pushability and resistance to buckling while still retaining relatively isotropic properties in bending. In other embodiments, annular segment widths and rotational angles can be varied (i.e., increased or decreased).

When the tubular member 26 is used as the center support shaft in a single lumen balloon catheter 10 as shown in FIGS. 1-3, the plurality of slots 28 allows rapid balloon inflation and deflation. The slots 28 are spaced and sized to create an extremely porous structure that allows rapid inflation and deflation from the lumen 30 of the tubular member 26 into the balloon 14. The ease of inflation and deflation enable the use of higher contrast medium, which enhances balloon visibility under fluoroscopy. The slot configuration also provides good axial strength (in tension and compression) as well as kinking and ovalization resistance when navigating tortuous vasculature. Further, tracking of the balloon catheter 10 is improved by varying the bending stiffness of the tubular member 26 such that it is softer at its distal end. Moreover, the tubular member 26 is more resistant to bowing and buckling during balloon inflation and deflation.

During inflation of compliant balloons it is possible for compressive forces to be created along the center shaft of the balloon. Traditional single lumen balloon catheters utilize a plastic shaft with holes drilled in it for fluid passage. The shaft must be stiff enough to resist buckling yet soft enough to track smoothly through tortuous vasculature. A simple plastic tube is not easily modified to vary stiffness along its length and is also susceptible to local buckling. The disclosed structure is highly kink resistant and easily varied in stiffness by changing beam heights, cutwidths, cut spacing, wall thickness, etc. Column buckling (Euler buckling), regardless of end constraints, is linearly proportional to bending stiffness and varies inversely with column length squared. Thus by stiffening the proximal portion of a shaft and softening the distal end, it is possible to create a net gain in buckling strength while retaining a soft distal tip, particularly for longer and larger balloon sizes (critical for atraumatic tracking). Alternatively, softening the stiffness profile of the entire shaft for shorter and smaller balloons to create maximum distal flexibility may provide better tracking.

Tubular member 26 and/or other components of balloon catheter 10 may be made from a metal, metal alloy, polymer (some examples of which are disclosed below), a metal-polymer composite, ceramics, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, the entire disclosures of which are incorporated herein by reference, as though set forth in full. Other suitable materials may include ULTANIUM™ (available from NeoMetrics) and GUM METAL™ (available from Toyota). In some other embodiments, a superelastic alloy, for example a superelastic nitinol can be used to achieve desired properties.

In at least some embodiments, portions or all of tubular member 26 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of balloon catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of balloon catheter 10 to achieve the same result.

In some embodiments, a degree of MRI compatibility is imparted into balloon catheter 10. For example, to enhance compatibility with Magnetic Resonance Imaging (MRI) machines, it may be desirable to make tubular member 26, or other portions of the balloon catheter 10, in a manner that would impart a degree of MRI compatibility. For example, tubular member 26, or portions thereof, may be made of a material that does not substantially distort the image and create substantial artifacts (artifacts are gaps in the image). Certain ferromagnetic materials, for example, may not be suitable because they may create artifacts in an MRI image. Tubular member 26, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

The entire balloon catheter 10 can be made of the same material along its length, or in some embodiments, can include portions or sections made of different materials. In some embodiments, the material used to construct balloon catheter 10 is chosen to impart varying flexibility and stiffness characteristics to different portions of balloon catheter 10. For example, proximal section 18 and distal section 20 of balloon catheter 10 may be formed of different materials, for example materials having different moduli of elasticity, resulting in a difference in flexibility. In some embodiments, the material used to construct proximal section 18 can be relatively stiff for pushability and torqueability, and the material used to construct distal section 20 can be relatively flexible by comparison for better lateral trackability and steerability. For example, proximal section 18 can be formed of polyimide shaft and/or doped polytetrafluoroethylene (PTFE) reinforced with 304v stainless steel wire or ribbon variable pick braiding or variable pitch cross wounding and distal section 20 can be formed with multidurometer polymeric outer layer such as PEBAX® over variable pick/pitch reinforced structure.

In embodiments where different portions of balloon catheter 10 are made of different materials, the different portions can be connected using any suitable connecting techniques and/or with a connector. For example, the different portions of balloon catheter 10 can be connected using welding (including laser welding/bonding), soldering, brazing, adhesive, thermal bonding or the like, or combinations thereof. These techniques can be utilized regardless of whether or not a connector is utilized. The connector may include any structure generally suitable for connecting portions of a balloon catheter. One example of a suitable structure includes a structure such as a hypotube or a coiled wire which has an inside diameter sized appropriately to receive and connect to the ends of the proximal portion and the distal portion. Essentially any suitable configuration and/or structure can be utilized for connecting various portions of the balloon catheter 10 including those connectors described in U.S. Pat. Nos. 6,918,882 and 7,071,197 and/or in U.S. Pat. No. 7,618,379, the entire disclosures of which are incorporated herein by reference, as though set forth in full.

FIGS. 7A-7C depict portions of various tubular members 26 that is not configured to underlie a balloon 14. A polymer layer 40 is disposed over each of the portions of the respective tubular members 26. The polymer layers 40 may be disposed over all (as shown in FIGS. 7A-7C) or most of the portions of the respective tubular members 26, thereby sealing all or most of the slots 28a-28d in the portions of the respective tubular members 26.

FIG. 7A, depicts a prior art polymer layer 40, which is laminated over the outer surface of the tubular member 26 portion. The polymer layer 40 forms a substantially consistent annular cross-section along the portion of the tubular member 26, thereby defining a generally smooth outer surface for the balloon catheter 10 that incorporates the tubular member 26. The polymer layer 40 according to this prior art design includes slot-overlaying segments 42a-42d, which are stretched taut over respective slots 28a-28d by the lamination process. As a result, when the tubular member 26 is flexed in one direction, the slot-overlaying segments 42a-42d on the other side of the tubular member 26 is stretched. The slot-overlaying segments 42a-42d resist stretching, thereby resisting flexure of the tubular member 26 and effectively increasing the stiffness of the tubular member 26. As discussed above, stiffness is an undesirable characteristic of tubular members 26.

Figure 10:
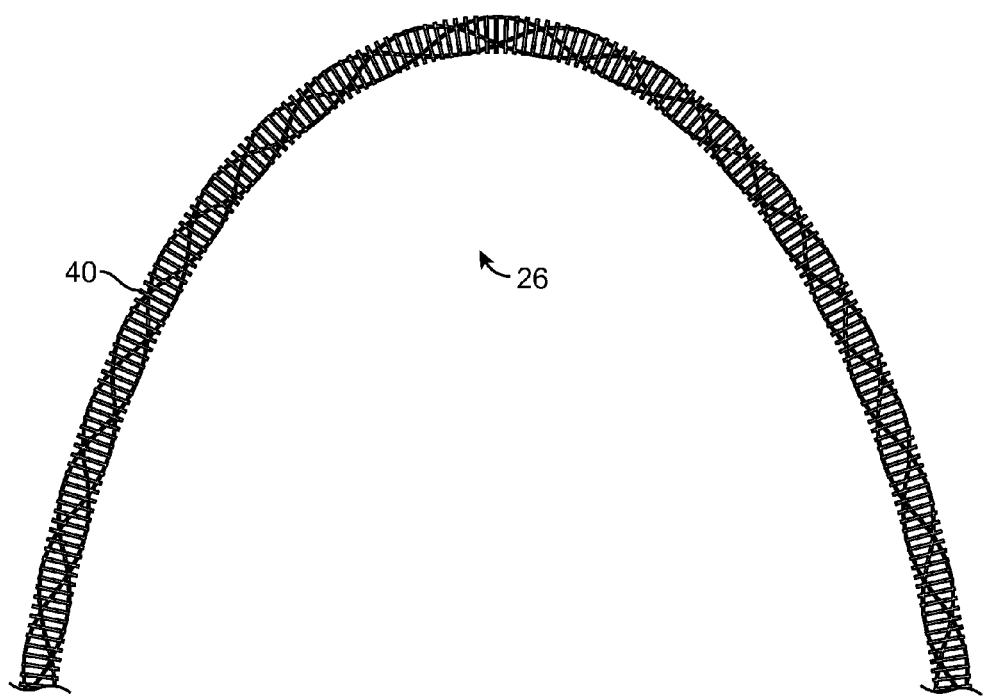
FIG. 10 is a perspective view of the balloon support shaft of FIG. 9 in a bent configuration.

In the embodiment shown in FIG. 7B, the polymer layer 40 includes slot-overlaying segments 42a-42d, which form invaginations that are longer than the respective slots 28a-28d that they overlay and invert into those slots 28a-28d. As used in this application, "invagination" means a portion of a surface that deviates from the plane of the surface in any direction. For instance, invaginations 42a-42d of a polymer layer 40 over a tubular member 26 can extend both radially inward (FIG. 7B) and outward (FIG. 7C) from the longitudinal axis of the tubular member 26. The slot-overlaying invaginations 42a-42d form annular pockets on the outer surface of the tubular member 26. As a result, the tubular member 26 can bend to a moderate degree without stretching the slot-overlaying invaginations 42a-42d. Instead, the slot-overlaying invaginations 42a-42d on the opposite side of the tubular member 26 from the direction of bending lengthens by straightening the section that is inverted into the slot 28a-28d, as shown in FIGS. 6 and 10. Accordingly, within the limits allowed by straightening of the slot-overlaying invaginations 42a-42d, the polymer layer 40 depicted in FIG. 7B exerts a negligible effect on the stiffness and does not substantially impede the flexibility of the tubular member 26. Another embodiment of a tubular member 26 with a polymer layer 40 that partially inverts into slots 28 is shown in perspective view in FIG. 11.

Figure 12:
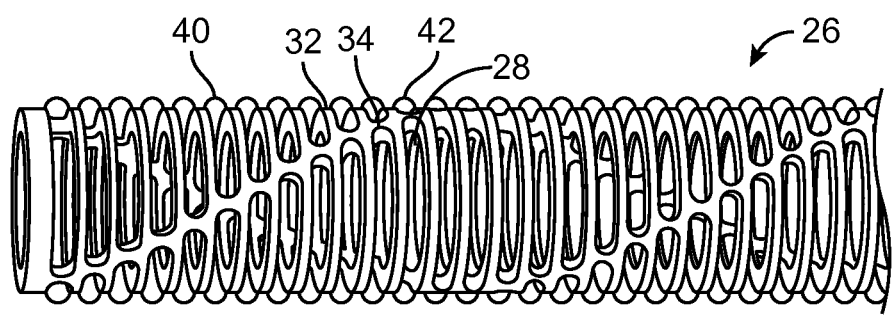

In the embodiment shown in FIG. 7C, the polymer layer 40 includes slot-overlaying invaginations 42*a*-42*d*, which are longer than the respective slots 28*a*-28*d* that they overlay and extend radially outward from the surface of the tubular member 26 above those slots 28*a*-28*d*. The slot-overlaying invaginations 42*a*-42*d* form annular bellows on the outer surface of the tubular member 26. As a result, the tubular member 26 can bend to a moderate degree without stretching the slot-overlaying invaginations 42*a*-42*d*. Instead, the slot-overlaying invaginations 42*a*-42*d* on the opposite side of the tubular member 26 from the direction of bending lengthens by straightening the section that is extends above the slot 28*a*-28*d*, as shown in FIGS. 6 and 10. Accordingly, within the limits allowed by straightening of the slot-overlaying invaginations 42*a*-42*d*, the polymer layer 40 depicted in FIG. 7C exerts a negligible effect on the stiffness and does not substantially impede the flexibility of the tubular member 26. Another embodiment of a tubular member 26 with a polymer layer 40 that partially extends radially outward from slots 28 is shown in perspective view in FIG. 12.

Figure 7D:
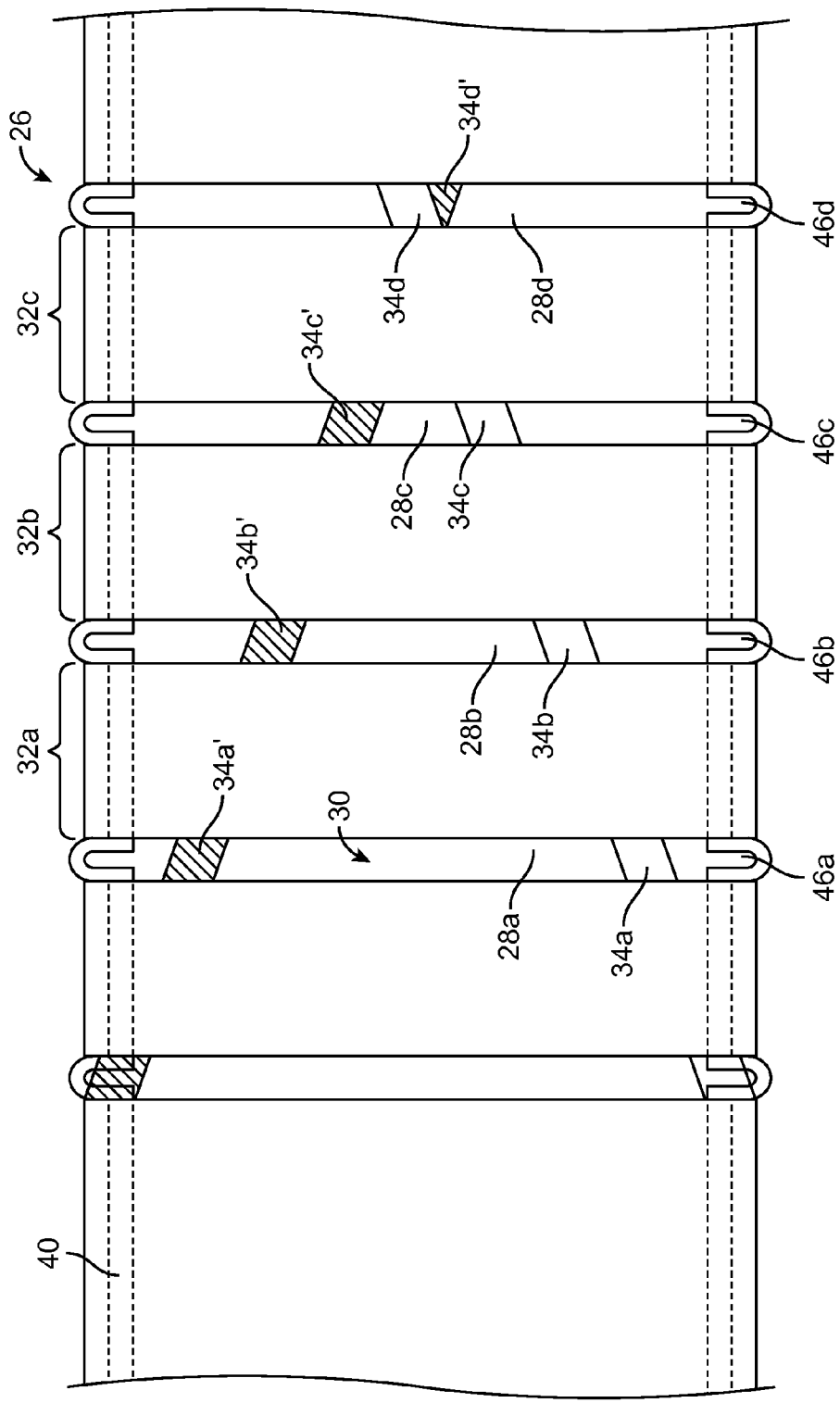

In the embodiment shown in FIG. 7D, the polymer layer 40 includes slot-underlying segments 46*a*-46*d*, which form invaginations that are longer than the respective slots 28*a*-28*d* that they underlie, and which extend radially outward from the inner surface of the tubular member 26 below slots 28*a*-28*d* and into, and partially out of, those slots 28*a*-28*d*. The slot-underlying invaginations 46*a*-46*d* form annular bellows in the respective slots 28*a*-28*d*, and partially on the outer surface of the tubular member 26. As a result, the tubular member 26 can bend to a moderate degree without stretching the slot-underlying invaginations 46*a*-46*d*. Instead, the slot-underlying invaginations 46*a*-46*d* on the opposite side of the tubular member 26 from the direction of bending lengthens by straightening the section that is extends above the slot 28*a*-28*d*, as shown in FIGS. 6 and 10. Accordingly, within the limits allowed by straightening of the slot-underlying invaginations 46*a*-46*d*, the polymer layer 40 depicted in FIG. 7D exerts a negligible effect on the stiffness of, and does not substantially impede the flexibility of, the tubular member 26.

Figure 7E:
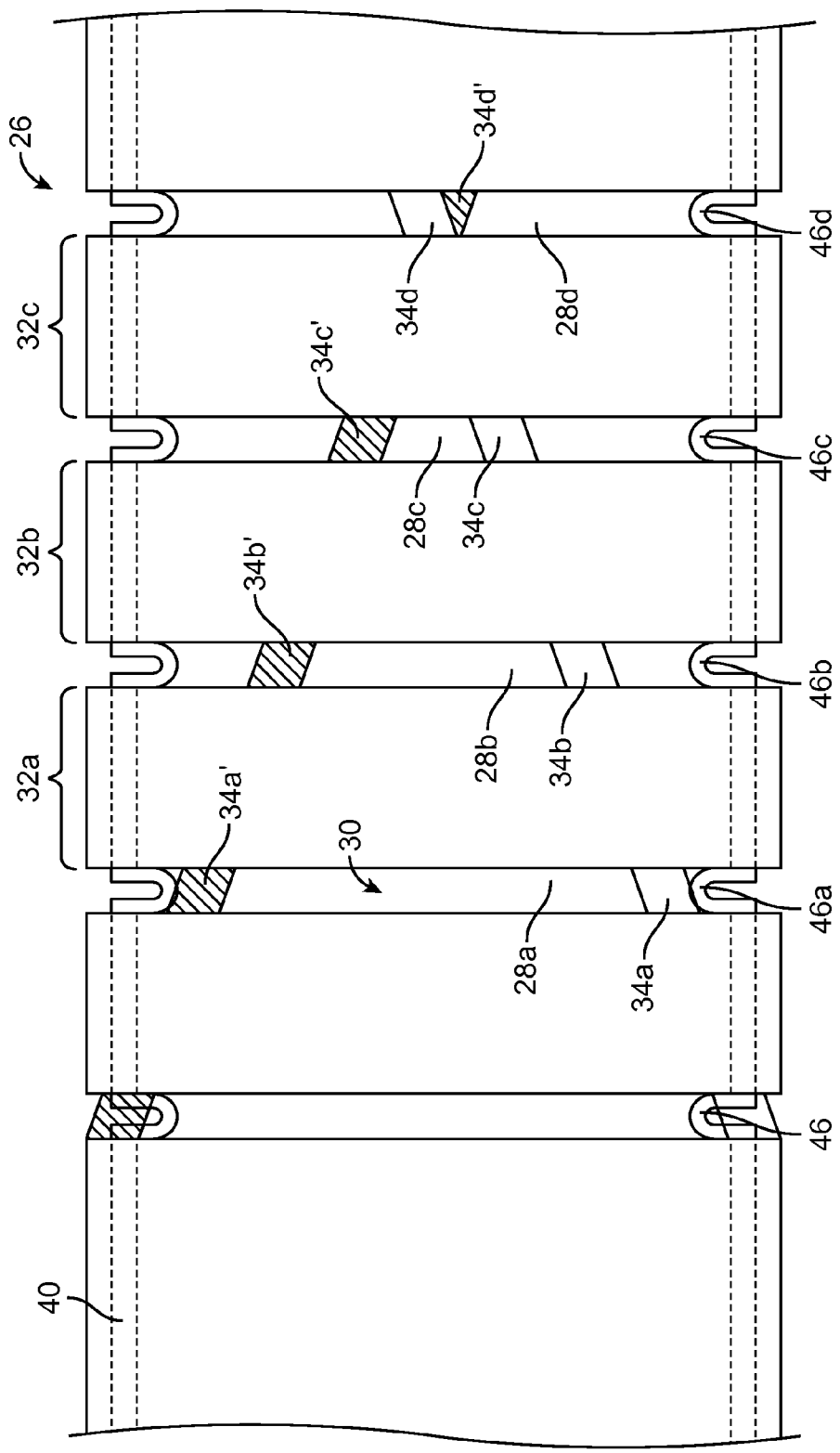

In the embodiment shown in FIG. 7E, the polymer layer 40 includes slot-underlying invaginations 46*a*-46*d*, which evert (i.e., extend) into the slots 28*a*-28*d* of the tubular member 26. In particular, the slot-underlying invaginations 46*a*-46*d* are longer than the respective slots 28*a*-28*d*, and form annular pockets in the respective slots 28*a*-28. As a result, the tubular member 26 can bend to a moderate degree without stretching the slot-underlying invaginations 46*a*-46*d*. Instead, the slot-underlying invaginations 46*a*-46*d* on the opposite side of the tubular member 26 of the direction of bending lengthen due to straightening of the section that is inverted into the slots 28*a*-28*d*, as shown in FIGS. 6 and 10. Accordingly, within the limits allowed by straightening of the slot-underlying invaginations 46*a*-46*d*, the polymer layer 40 depicted in FIG. 7E exerts a negligible effect on the stiffness, and does not substantially impede the flexibility, respectively, of the tubular member 26.

The layer 40 may be made from a polymer or any other suitable material. Some examples of suitable polymers may include polyp-xylylene) ("parylene"), low density polyethylene (LDPE), linear low density polyethylene (LLDPE), polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the layer 40 can be blended with a liquid crystal polymer (LCP). For example, the mixture can contain up to about 6% LCP.

In some embodiments, the exterior surface of the balloon catheter 10 (including, for example, the exterior surface of the tubular member 26) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the layer 40, or in embodiments without a layer over portion of the tubular member, or other portions of device 10. Alternatively, the layer 40 may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference, as though set forth in full.

The layer 40 may be formed as described below. The layer 40 may have a uniform stiffness or a gradual reduction in stiffness from the proximal end to the distal end thereof. The gradual reduction in stiffness may be continuous or may be stepped as by fusing together separate extruded tubular segments. The layer 40 may be impregnated with radiopaque filler materials such as barium sulfate, bismuth, or tungsten to facilitate radiographic visualization. Those skilled in the art will recognize that these materials can vary widely without deviating from the scope of the present invention.

The distal portion of the balloon 14 is attached to the distal end of the tubular member 26 and to the distal flexible tip distal of the inflation ports/irrigation channels. The balloon 14 is positioned on the tubular member 26 such that the balloon 14 overlays a portion of the tubular member 26 having slots 28 formed therein. However, other portions of the tubular member 26 may also have slots 28 formed therein to modify the flexibility of the tubular member 26. The balloon 14 may be made of a highly compliant material that elastically expands upon pressurization. Because the balloon 14 elastically expands from the deflated state to the inflated state, the balloon 14 has an extremely low profile in the deflated state and may be used without folding the balloon. The balloon may be formed of silicone, urethane polymer, or an extruded thermoplastic elastomers polyisoprene rubber such as a 70A, 65A, 60A, 52A, 45A, 42A, 40A, 32A, 30A, 25A, 15A, 12A, and 5A durometer hydrogenated polyisoprene rubber, which is commercially available under the trade name Chronoprene™ and Mediprene™ from AdvanSource Biomaterials, Inc. and Elasto, respectively. Hydrogenated polyisoprene provides a balloon having superior performance and manufacturing attributes. In particular, hydrogenated polyisoprene may be processed with standard polyolefin processing equipment to obtain balloon tubing having a wall thickness of approximately 0.001 inches to 0.010 inches and a corresponding inside diameter of approximately 0.016 inches to 0.058 inches. Such tubing produces balloons having a nominal inflated outside diameter of approximately 3.0 mm to 7.5 mm. The highly compliant balloon preferably elastically expands at pressures less than 1.0 ATM. The highly compliant balloon may have a pressure compliance of 2.0 mm/ATM or more at pressures less than 2.0 ATM. The highly compliant balloon may have a volumetric compliance of approximately 0.3 mm per 0.01 ml to 0.5 mm per 0.01 ml at pressures less than 2.0 ATM, for balloons having a nominal diameter of approximately 3.5 mm and a length of approximately 10 mm to 30 mm. The ends of the balloon are attached to the tubular member 26 and the flexible distal tip using conventional bonding means such as thermal bonding using a hot jaw, hot air source, or a laser. The tubular member 26, excluding the balloon 14 and distal flexible tip, can be coated with hydrophilic coatings such as Hydropass, Hydrolene or Bioslide.

Figure 4:
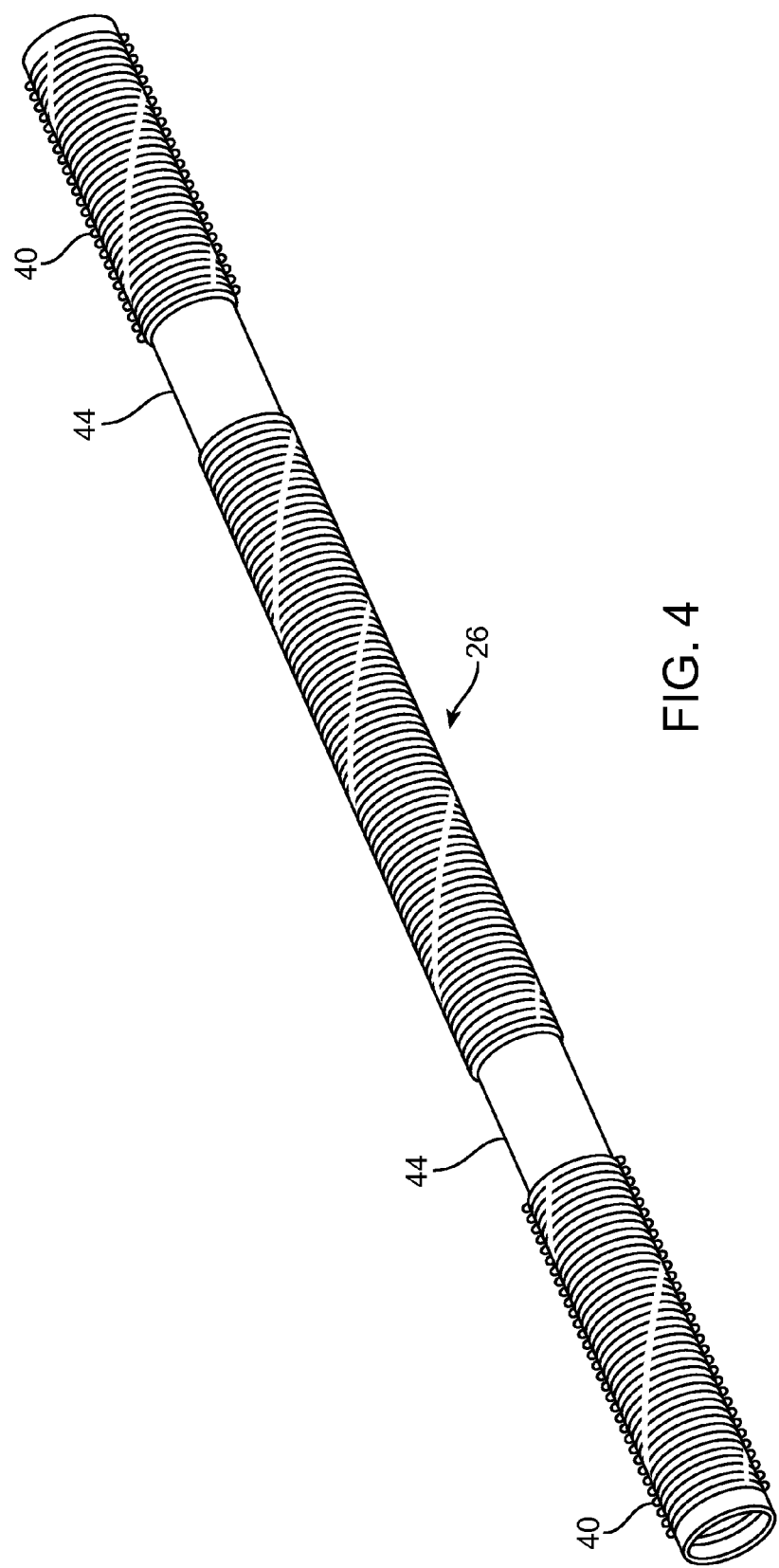
FIG. 4 is a perspective view of a balloon support shaft constructed according to one embodiment.
Figure 5:
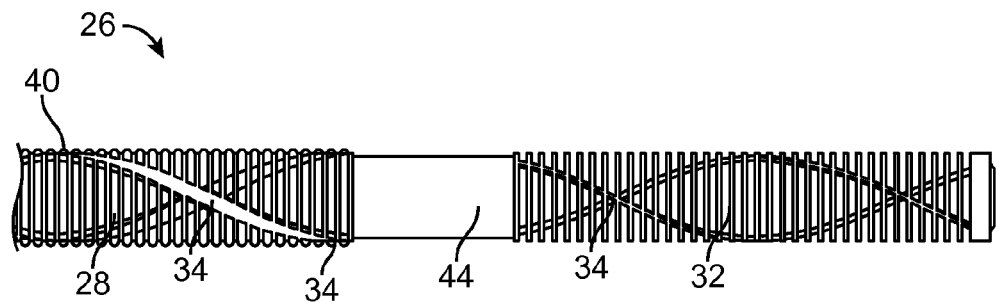
FIG. 5 is a perspective view of a balloon support shaft constructed according to one embodiment.

As shown in FIG. 4, marker bands 44 are mounted on the tubular member 26. FIG. 5 shows the recessed wide annular segment 32 configured to hold the cylindrical marker band 44 in FIG. 4. Further, the annular segments 32 on either side of the recessed wide annular segment 32 are raised relative to the recessed wide annular segments 32 (not beyond the outer diameter of the tubular member 26) to retain the marker band 44 therein. The marker band 44 may be made of a full band, slit band, or coil wound of round or ribbon wire made of materials like Platinum/Tungsten, Gold. The marker band 44 may also be made from a low durometer polymer or any other suitable materials impregnated with radiopaque filler materials such as Barium Sulfate, Bismuth or Tungsten to facilitate radiographic visualization. Some examples of suitable polymers may include low density polyethylene (LDPE), linear low density polyethylene (LLDPE), elastomeric polyamides, block polyamide/ethers, polyether block amide (PEBA, for example available under the trade name PEBAX®).

Figure 14:
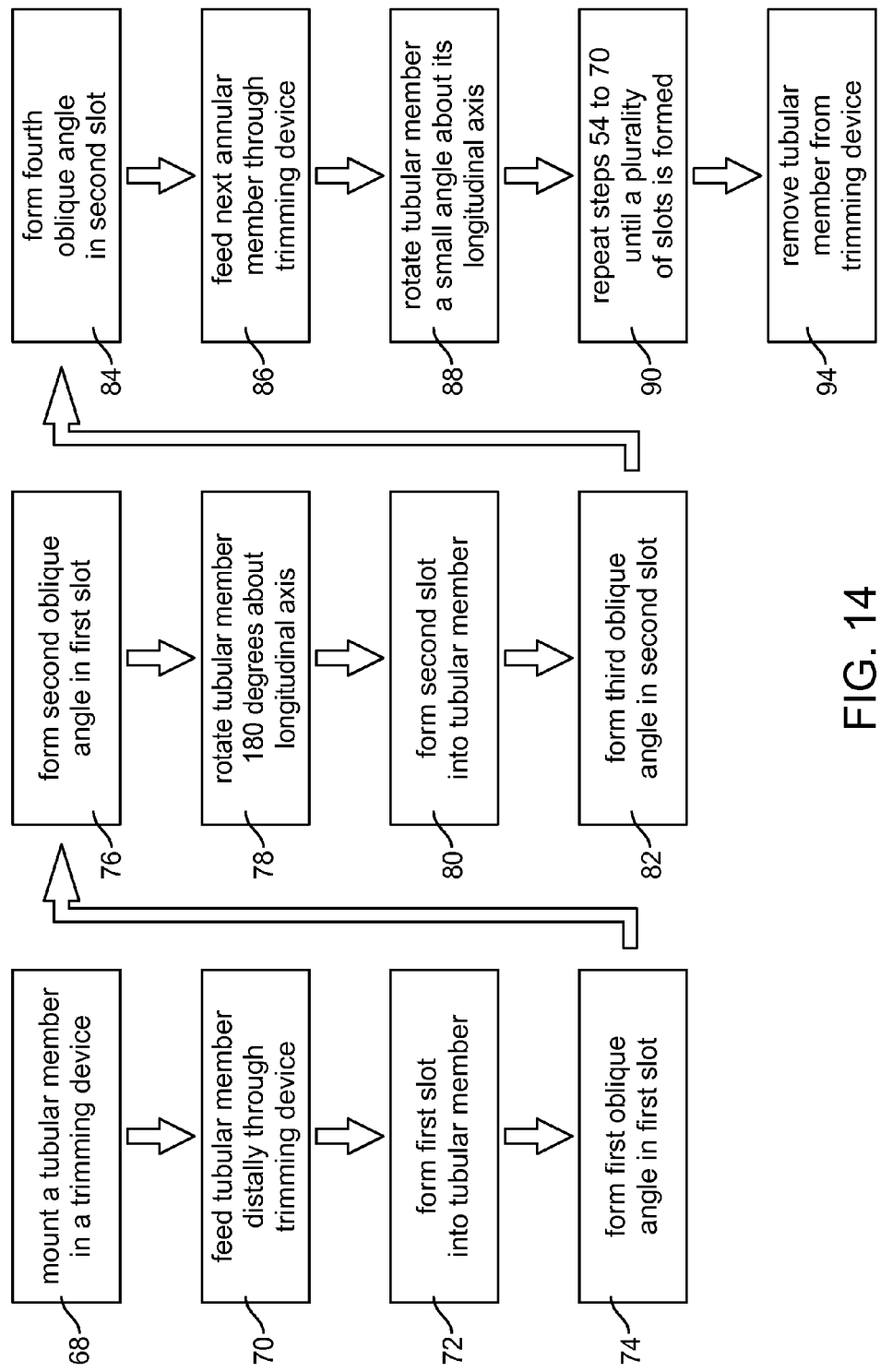
FIG. 14 is a flow chart showing a method of manufacturing a balloon support shaft according to one embodiment.

As shown in FIG. 14, a balloon catheter 10 may be manufactured by first mounting a tubular member 26 in a trimming device (step 50). Next, a first annular segment 32 of the tubular member 26 is fed distally through the trimming device (step 52). Then, a first slot 28 is formed into the tubular member 26 proximal of the first annular segment 32, e.g. by laser cutting (step 54). Subsequently, a first oblique angle between the longitudinal surface of a beam 34 formed by the first slot 28 and the transverse surface of an adjacent annular segment 32 is formed at a first end of the first slot 28 (step 56), as shown in FIG. 8.

Next, a second oblique angle between the longitudinal surface of the beam 34 and the transverse surface of the adjacent annular segment 32 is formed at a second end of the first slot 28 (step 58). Then, the tubular member 26 is rotated 180 degrees about its longitudinal axis (step 60). Subsequently, a second slot 28 is formed into the tubular member 26 proximal of the first annular segment 32 (step 62).

Next, a third oblique angle between the longitudinal surface of the beam 34 and the transverse surface of the adjacent annular segment 32 is formed at a first end of the second slot 28 (step 64). Then, a fourth oblique angle between the longitudinal surface of the beam 34 and the transverse surface of an adjacent annular segment 32 is formed at a second end of the second slot 28 (step 66). Subsequently, the next annular segment 32 of the tubular member 26 is fed distally through the cutting device (step 68).

Next, tubular member is rotated a small angle (about eight degrees) about its longitudinal axis (step 70). Step 54 to step 70 are repeated until a plurality of slots 28 have been cut into the tubular member 26 (step 72), at which time the tubular member 26 is removed from the trimming device (step 74). Finally, when making a balloon catheter 10, a balloon 14 is attached to the tubular member 26 so that the balloon 14 defines a balloon lumen in communication with at least one slot 28.

As shown in FIGS. 7A-7C, 11 and 12, portions of tubular member 26 not underlying balloons 14 is covered with a polymer layer 40. The polymer layer 40 can be added to the tubular member 26 either before or after the balloon 14 is attached to the tubular member 26. Embodiments of methods for adding such a polymer coating/layer 40 to a tubular member 26 are depicted in FIGS. 15-23. While the embodiments described herein involve tubular member 26 forming part of a balloon catheter 10, and having slots 28 and a polymer layer 40, the methods describe herein also apply to coating any tubular member 26 having openings 28 therein. These coated tubular members 26 can then be further processed to form any elongate flexible medical device.

Figure 15:
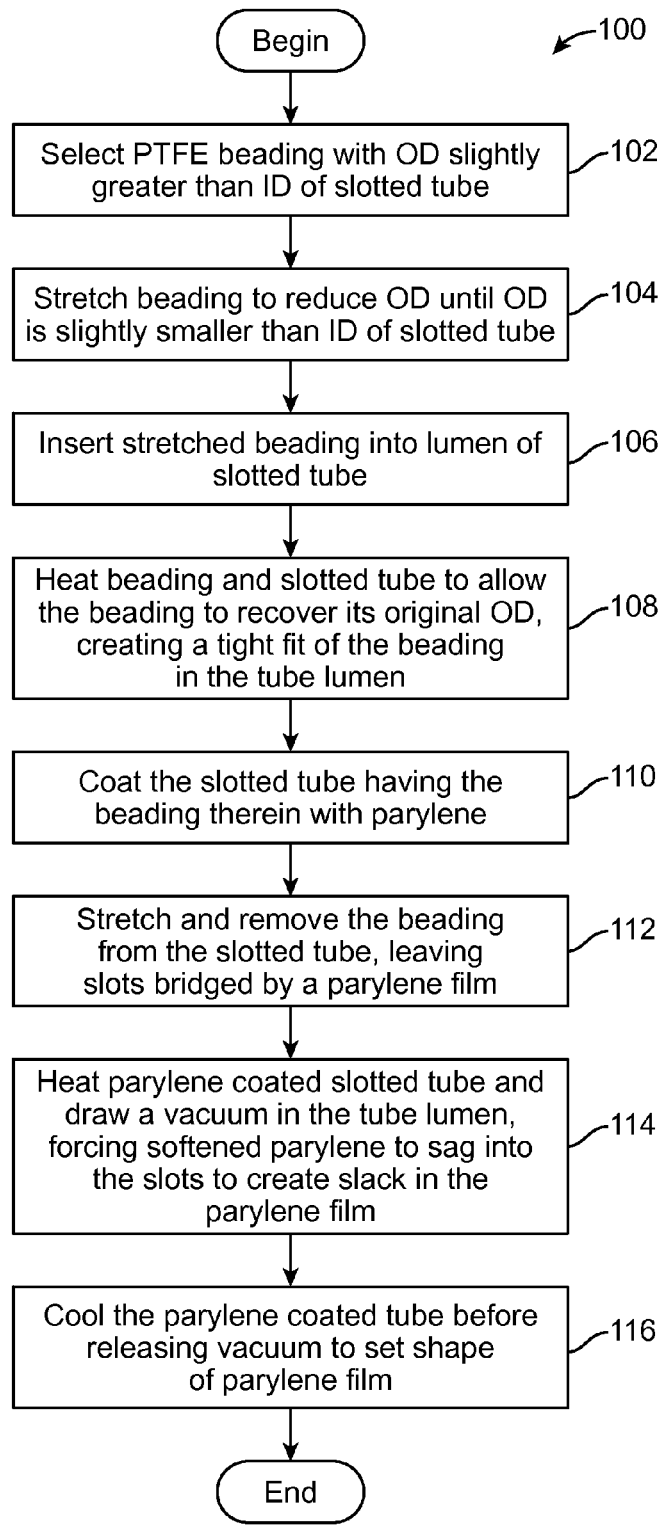
FIGS. 15-23 are flowchart showing various methods of coating a tubular member with a polymer according to respective embodiments of the disclosed inventions.

FIG. 15 depicts a method 100 for adding a polymer coating/layer 40 to a tubular member 26. At step 102, a rod (e.g., a PTFE or similar polymer beading), with an outer diameter slightly larger than the inner diameter of the tubular member 26, is selected. At step 104, the rod is stretched at room temperature to reduce its outer diameter until that outer diameter is slightly smaller than the inner diameter of the tubular member 26. At step 106, the stretched rod (with the reduced outer diameter) is inserted into the lumen 30 of the tubular member 26.

At step 108, the tubular member 26 and the rod are heated (e.g., at 250-300° C. for approximately 1 hour) to allow the rod to recover some portion of its original outer diameter. Because that original diameter is slightly larger than the inner diameter of the tubular member 26, the recovered/expanded rod forms a tight fit in the lumen 30 of the tubular member 26, sealing substantially all of the slots 28 of the tubular member 26. At step 110, the tubular member 26 with the recovered/expanded rod inserted therein is coated with a polymer (e.g., parylene). At step 112, the rod is stretched axially to reduce its outer diameter and removed from the tubular member 26, leaving a polymer coating 40 over the tubular member 26, including over substantially all of the slots 28 therein.

Figure 11:
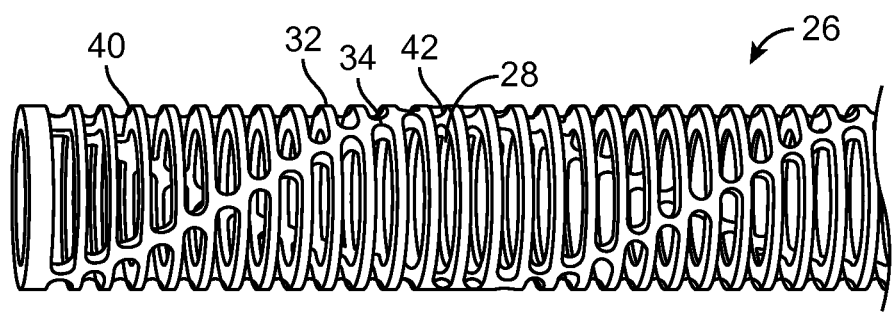
FIGS. 11, 12 and 13A-13C are detailed perspective views of balloon support shafts constructed according to various embodiments of the disclosed inventions.

At step 114, the tubular member 26 and the polymer coating 40 disposed thereon are heated until the polymer coating 40 reaches a temperature above its softening point (approximately 290° C. for parylene). Further at step 114, while the polymer coating 40 is heated to a temperature above its softening point, a vacuum is drawn in the lumen 30 of the tubular member 26. The vacuum pulls the slot-overlaying segments 42 of the polymer coating into the slots 28 thereby forming invaginations. At step 116, the tubular member 26 and the polymer coating 40 are cooled to below the softening point of the polymer coating 40, while the vacuum is maintained, in order to set the shape of the polymer coating 40. This set shape includes slot-overlaying invaginations 42 that invert into the slots 28, as shown in FIGS. 7B and 11. After the shape of the polymer coating 40 is set, the vacuum can be released at the coated tubular member 26 is ready for further processing to form a medical device.

Figure 16:
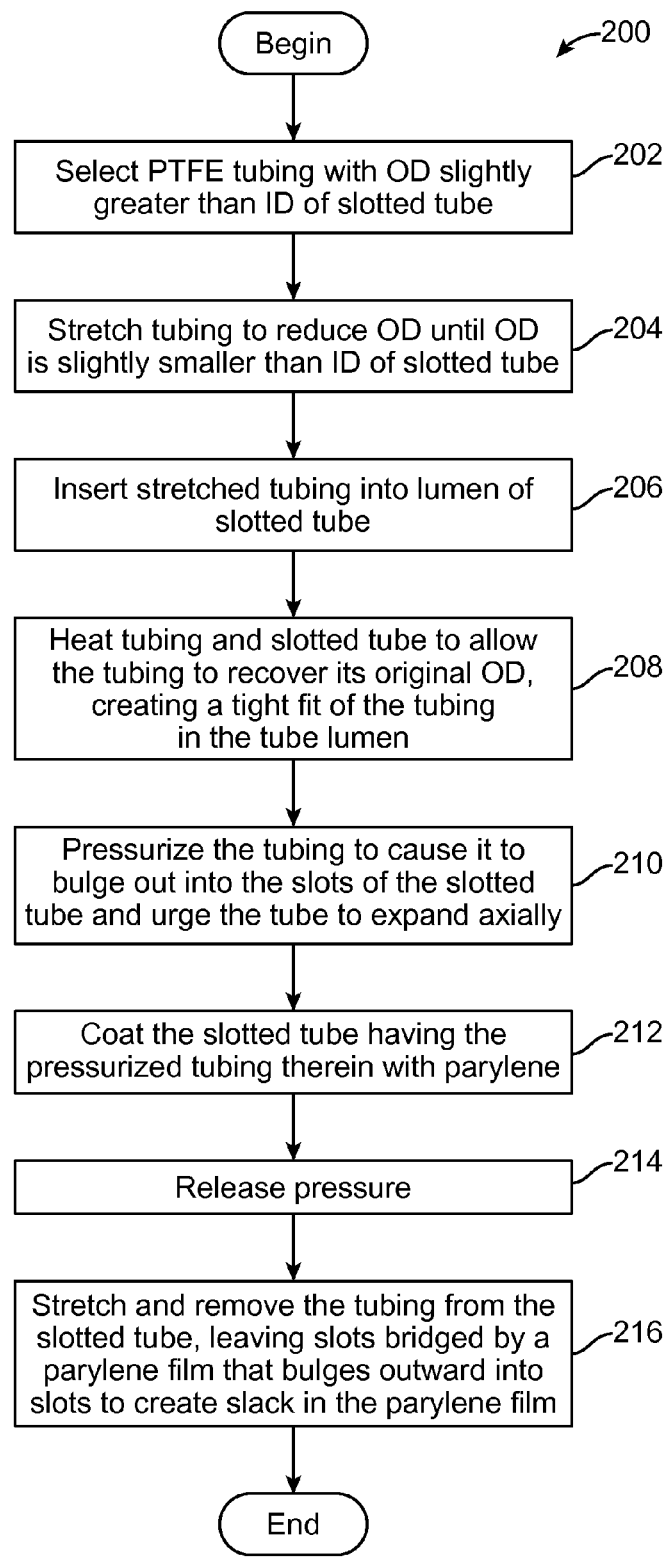

FIG. 16 depicts another method 200 for adding a polymer coating/layer 40 to a tubular member 26. At step 202, a tube (e.g., a PTFE or similar polymer tube), with an outer diameter slightly larger than the inner diameter of the tubular member 26, is selected. At step 204, the tube is stretched to reduce its outer diameter until that outer diameter is slightly smaller than the inner diameter of the tubular member 26. At step 206, the stretched tube (with the reduced outer diameter) is inserted into the lumen 30 of the tubular member 26.

At step 208, the tubular member 26 and the tube are heated to allow the tube to recover its original outer diameter. Because that original diameter is slightly larger than the inner diameter of the tubular member 26, the recovered/expanded tube forms a tight fit in the lumen 30 of the tubular member 26, sealing substantially all of the slots 28 of the tubular member 26. At step 210, the lumen of the recovered/expanded tube inserted into the tubular member 26 is pressurized to cause it to expand radially into the slots 28 of the tubular member 26. This step may be executed at an elevated temperature to facilitate radial expansion of the tube. Pressurizing the tube also urges the tubular member to expand axially. At step 212, the tubular member 26 with the recovered/expanded tube inserted therein is coated with a polymer (e.g., parylene). At step 214, the pressure in the tube is released, allowing the tube and the tubular member to return to their respective radially and axially contracted conditions. At step 216, the tube is stretched axially to reduce its outer diameter and removed from the tubular member 26, leaving a polymer coating 40 over the tubular member 26, including slot-overlaying invaginations 42 extending radially outward over substantially all of the slots 28 therein like those shown in FIGS. 7C and 12. After the tube is removed, the coated tubular member 26 is ready for further processing to form a medical device. Depending on the flexibility of the polymer tube and the thickness of the polymer coating 40, the resulting slot-overlaying invaginations 42 may bulge radially outward from the bottom of and into the respective slots 28.

Figure 17:
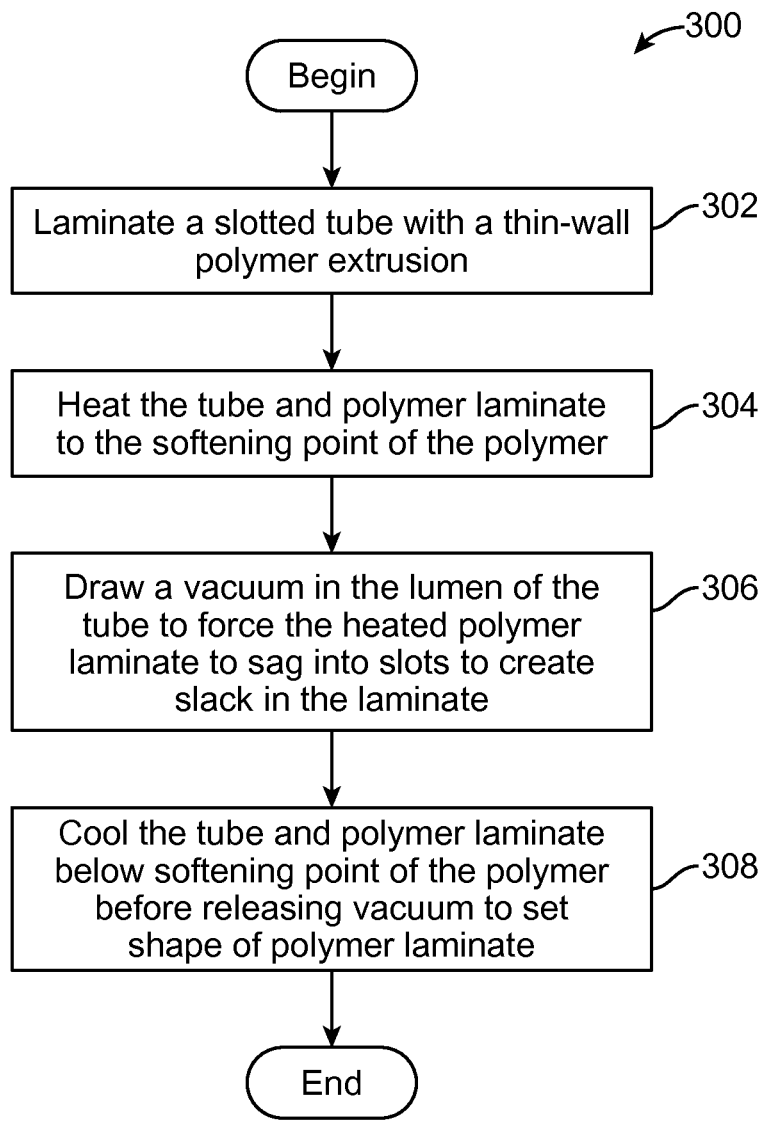

FIG. 17 depicts yet another method 300 for adding a polymer coating/layer 40 to a tubular member 26. At step 302, a tubular member 26 is laminated with a thin wall-polymer extrusion (e.g., a 0.0005" thick layer 40 of Tecothane™), forming a polymer coating/layer 40. At step 304, the tubular member 26 and the polymer laminate 40 are heated above the softening point of the polymer. At step 306, a vacuum is drawn in the lumen 30 of the tubular member 26, forcing the heated and softened polymer laminate 40 to extend radially inward (i.e., invert) into the slots 28 in the tubular member 26.

At step 308, the tubular member 26 and the polymer laminate 40 and cooled below the softening point of the polymer, while the vacuum is maintained, thereby setting the shape of the polymer laminate 40. This set shape includes slot-overlaying invaginations 42 that invert into the slots 28, as shown in FIGS. 7B and 11. After the shape of the polymer laminate 40 is set, the vacuum can be released, and the coated tubular member 26 is ready for further processing to form a medical device.

Alternatively, a tubular member 26 can be coated with a low-durometer polymer, such as a polyurethane, like Tecothane™. The low-durometer coating 40 should have minimal effect on the flexibility/stiffness of the tubular member 26, while sealing the slots 28 in the tubular member 26 Further, the polymer coating 40 will provide an improved substrate for additional hydrophilic coatings (compared to a bare metal or parylene coated surface).

Figure 18:
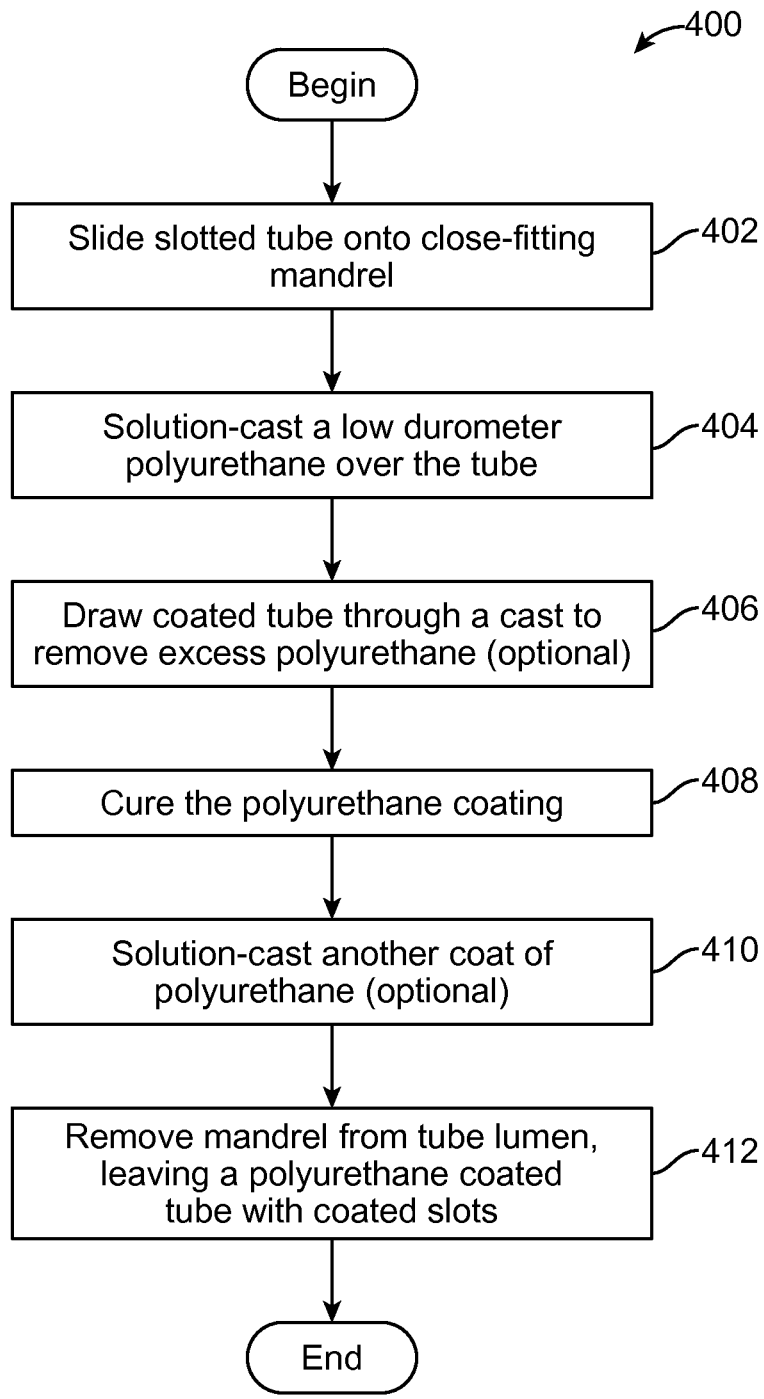

FIG. 18 depicts one embodiment of a method 400 for coating a tubular member 26 with a low-durometer polymer layer 40. At step 402, the tubular member 26 is mounted onto a close-fitting mandrel. A stretched-recovered polymer (e.g., PTFE) rod can be substituted for the close-fitting mandrel. The close-fitting mandrel effectively seals most of the slots 28 in the tubular member 26. At step 404, low durometer polyurethane (Tecothane™) is solution-cast onto the tubular member 26, to form a thin layer 40 (e.g., 0.0003" to 0.0005"). Solution-casting is also known as dip coating (to form a very thin layer 40) and films-casting. At optional step 406, the polyurethane coated tubular member 26 can be drawn through a cast to remove excess polyurethane.

At step 408, polyurethane coating is cured using known methods. At optional step 410, another low-durometer polymer layer 40 can be solution-cast on top of the first polyurethane layer 40 by repeating steps 404 to 408. At step 412, the mandrel (or PTFE rod) is removed from the lumen 30 of the tubular member 26. This process results in a tubular member 26 in which a significant portion of the slots 28 of the tubular member 26 are sealed with a low-durometer polymer. This tubular member 26 appears similar to the prior art tubular member 26 depicted in FIG. 7A, however the polymer layer 40 has a low-durometer, and therefore has minimal effect on the stiffness/flexibility of the tubular member 26. At this point, the coated tubular member 26 is ready for further processing to form a medical device.

Figure 19:
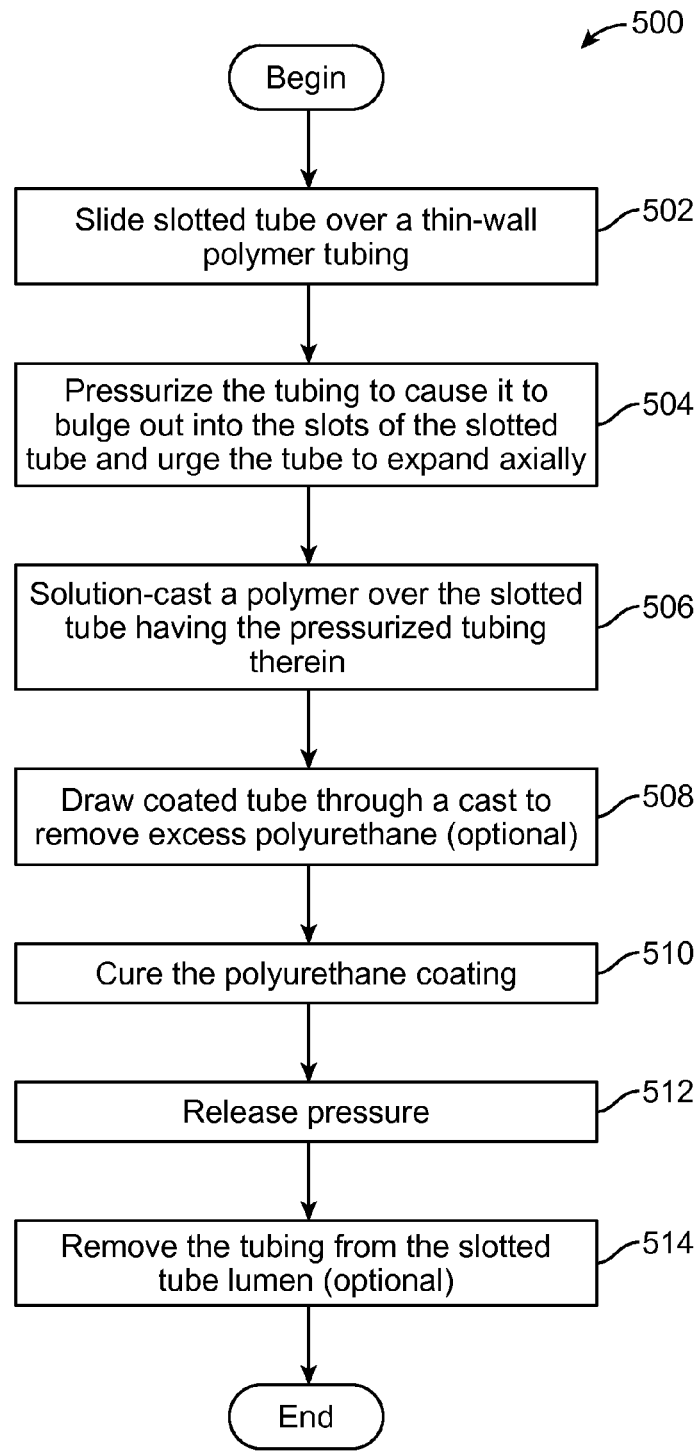

FIG. 19 depicts yet another embodiment of a method 500 for adding a polymer coating/layer 40 to a tubular member 26. At step 502, the tubular member 26 is slid onto a thin-wall polymer (e.g., PTFE or Chronopene™) tubing. At step 504, the lumen of the polymer tubing is pressurized to cause portions of the polymer tubing to expand into the slots 28 of the tubular member 26. Pressurizing the polymer tubing also causes the tubular member 26 to lengthen axially. At step 506, a low-durometer polyurethane (Tecothane™) is solution-cast onto the tubular member 26. At optional step 508, the polyurethane coated tubular member 26 can be drawn through a cast to remove excess polyurethane.

At step 510, polyurethane coating is cured using known methods. At optional step 512, the thin-wall polymer tubing is removed from the lumen 30 of the tubular member 26.

This process results in a tubular member 26 in which a significant portion of the slots 28 of the tubular member 26 are sealed with a low-durometer polymer. This tubular member 26 appears similar to the prior art tubular member 26 depicted in FIG. 7A, however the polymer layer 40 has a low-durometer, and therefore has minimal effect on the stiffness/flexibility of the tubular member 26. If the thin-wall polymer tubing is not removed an additional layer of polymer tubing would seal the slots 28. At this point, the coated tubular member 26 is ready for further processing to form a medical device.

Figure 20:
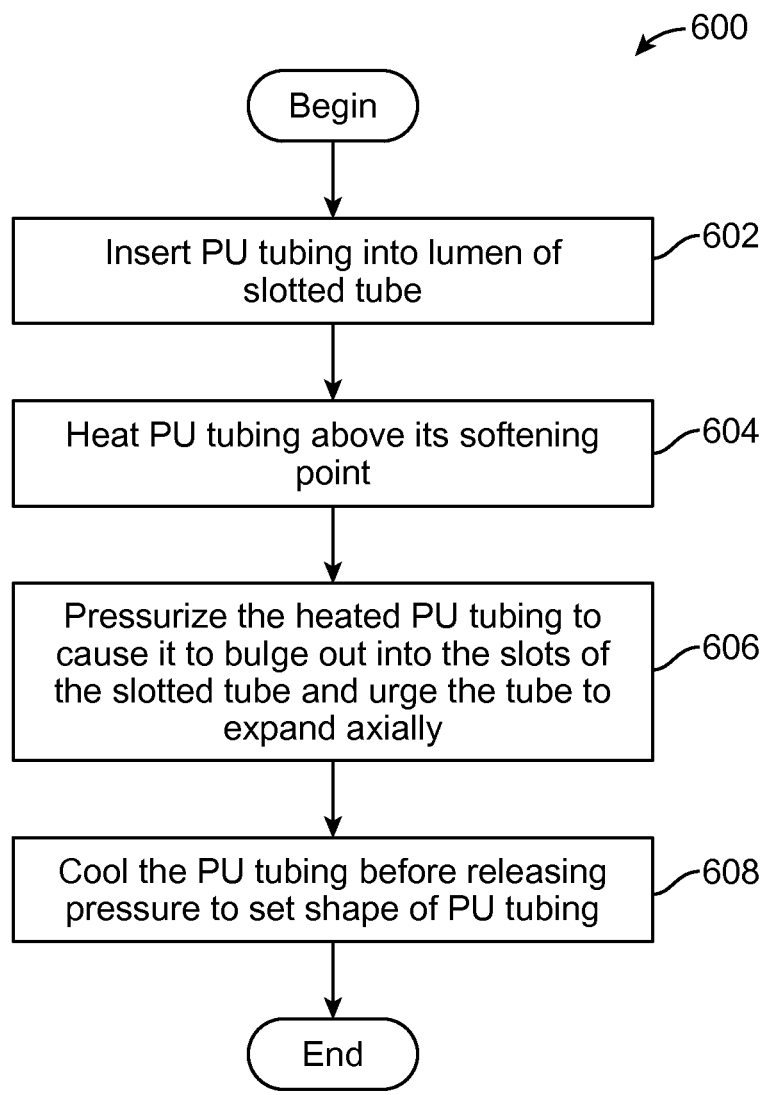

FIG. 20 depicts yet another method 600 for adding a polymer coating/layer 40 to a tubular member 26, according to yet another embodiment of the disclosed inventions. At step 602, a thin-wall, polymer tube (e.g., a 0.0005" thick layer 40 of Tecothane™) is inserted into the lumen 30 of a tubular member 26, forming a polymer coating/layer 40. At step 604, the tubular member 26 and the polymer tube are heated above the softening point of the polymer. At step 606, the lumen of the polymer tube is pressurized to cause portions of the polymer tube to expand radially into the slots 28 of the tubular member 26. Pressurizing the tube also urges the tubular member to expand axially.

At step 608, the tubular member 26 and the polymer tube are cooled below the softening point of the polymer, while the pressure is maintained, thereby setting the shape of the polymer coating/layer 40. This set shape includes slot-underlying invaginations 46 that evert into the and partially out of slots 28, as shown in FIG. 7D. After the shape of the polymer coating/layer 40 is set, the pressure can be released, and the coated tubular member 26 is ready for further processing to form a medical device.

Figure 21:
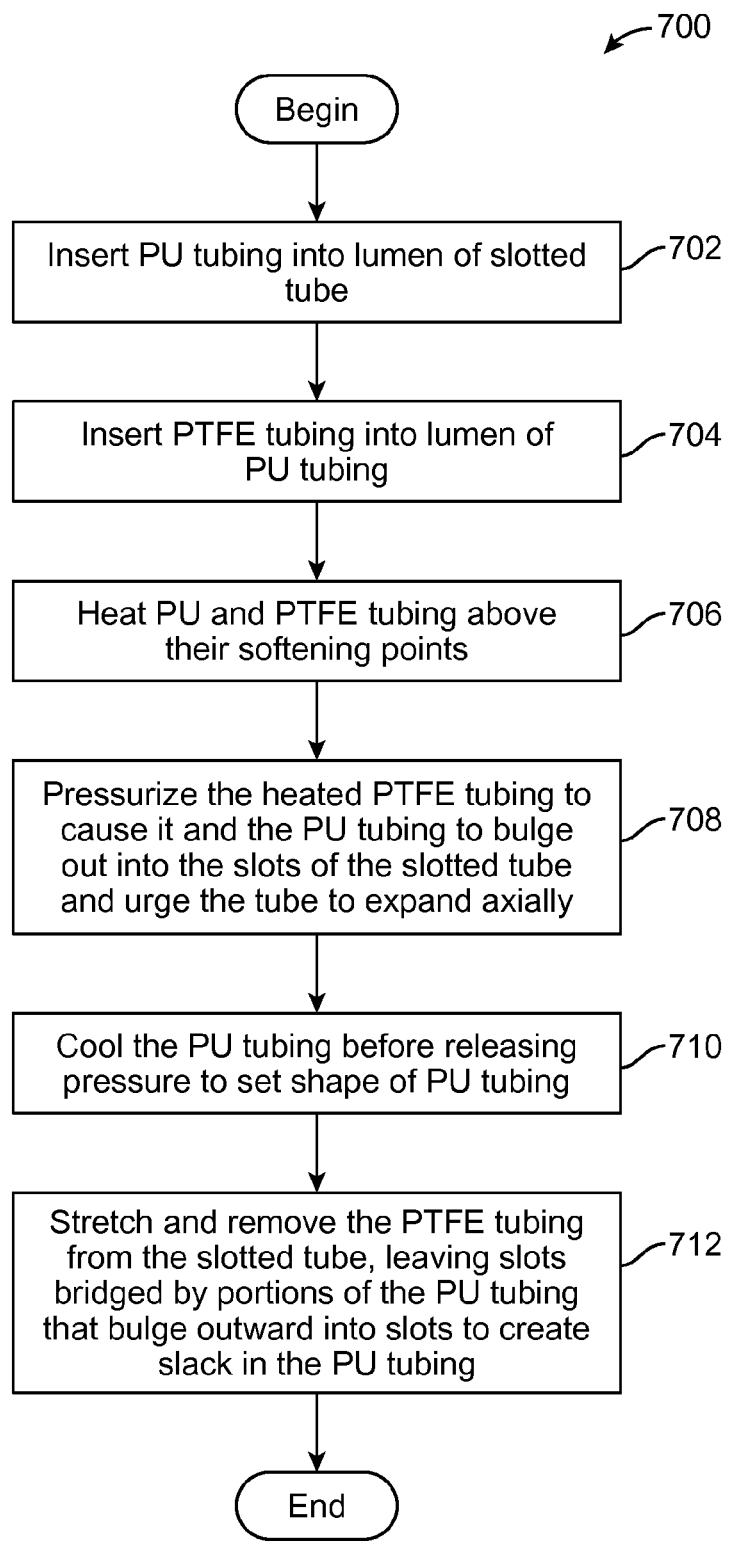

FIG. 21 depicts still another method 700 for adding a polymer coating/layer 40 to a tubular member, according to still another embodiment of the disclosed inventions. The method 700 depicted in FIG. 21 is a variation on the method 600 depicted in FIG. 20, in which a PTFE tube is used to expand the thin-wall, polymer into the slots 28 of the tubular member 26. At step 702, a thin-wall, polymer tube (e.g., a 0.0005" thick layer 40 of Tecothane™) is inserted into the lumen 30 of a tubular member 26, forming a polymer coating/layer 40. At step 704, a PTFE tube is inserted into the lumen of the thin-wall, polymer tube. At step 706, the tubular member 26, the polymer tube and the PTFE tube are heated above the softening point of the polymer and the PTFE. At step 708, the lumen of the PTFE tube is pressurized to cause portions of the PTFE tube and the polymer tube to expand radially into the slots 28 of the tubular member 26. Pressurizing the tubes also urges the tubular member to expand axially.

At step 710, the tubular member 26 and the polymer tube are cooled below the softening point of the polymer, while the pressure is maintained, thereby setting the shape of the polymer coating/layer 40. This set shape includes slot-underlying invaginations 46 that evert into the and partially out of slots 28, as shown in FIG. 7D. After the shape of the polymer coating/layer 40 is set, the pressure is released. At step 712, the PTFE tube is stretched and removed from the lumen of the polymer tube and the slotted tube 26. At that point, the coated tubular member 26 is ready for further processing to form a medical device.

Figure 22:
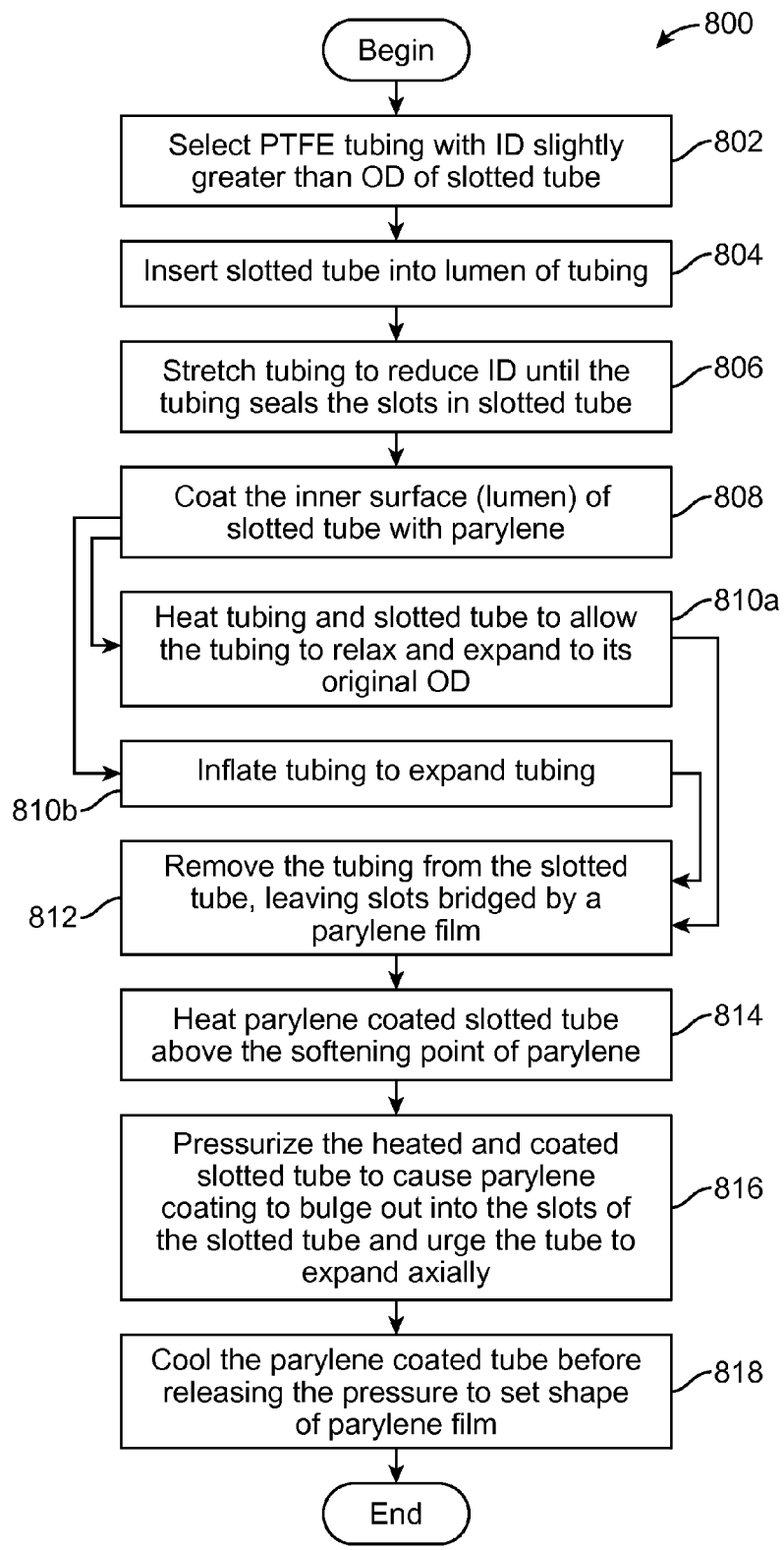

FIG. 22 depicts a method 800 for adding a polymer coating/layer 40 to a slotted tube 26, according to yet another embodiment of the disclosed inventions. At step 802, a polymer tubing (e.g., a PTFE or similar polymer tubing), with an inner diameter slightly larger than the outer diameter of the slotted tube 26, is selected. At step 804, the slotted tube 26 is inserted into the lumen of the polymer tubing. At step 806, the polymer tubing is stretched to reduce its inner diameter until the tubing seals the slots 28 in the slotted tube 26. At step 808, the inner surface (i.e., the lumen) of the slotted tube 26 is coated with a polymer (e.g., by parylene deposition).

Next, the polymer tubing is expanded for removal from the slotted tube 26 in one (or both) of two ways. In step 810a, the polymer tubing and the slotted tube 26 are heated to allow the tubing to relax and expand to its original inner diameter (i.e., slightly larger than the outer diameter of the slotted tube 26). Alternatively or additionally, the polymer tubing can be expanded by inflation, as described in step 810b. At step 812, the polymer tubing is removed from the slotted tube 26, leaving slots 28 bridged and sealed by a polymer coating 40 (i.e., a parylene film) on the inner surface of the slotted tube 26.

At step 814, the tubular member 26 and the polymer coating 40 disposed thereon are heated until the polymer coating 40 reaches a temperature above its softening point (approximately 290° C. for parylene). At step 816, while the polymer coating 40 is heated to a temperature above its softening point, the lumen 30 of the tubular member 26 (with the polymer coating 40 on its inner surface) is pressurized to cause portions of the polymer coating to expand radially into the slots 28 of the tubular member 26. Pressurizing the sealed tubular member 26 also urges the tubular member to expand axially.

At step 818, the tubular member 26 and the polymer coating 40 are cooled below the softening point of the polymer, while the pressure is maintained, thereby setting the shape of the polymer coating/layer 40. This set shape includes slot-underlying invaginations 46 that evert into the and partially out of slots 28, as shown in FIG. 7D. After the shape of the polymer coating/layer 40 is set, the pressure is released, and the coated tubular member 26 is ready for further processing to form a medical device.

Figure 23:
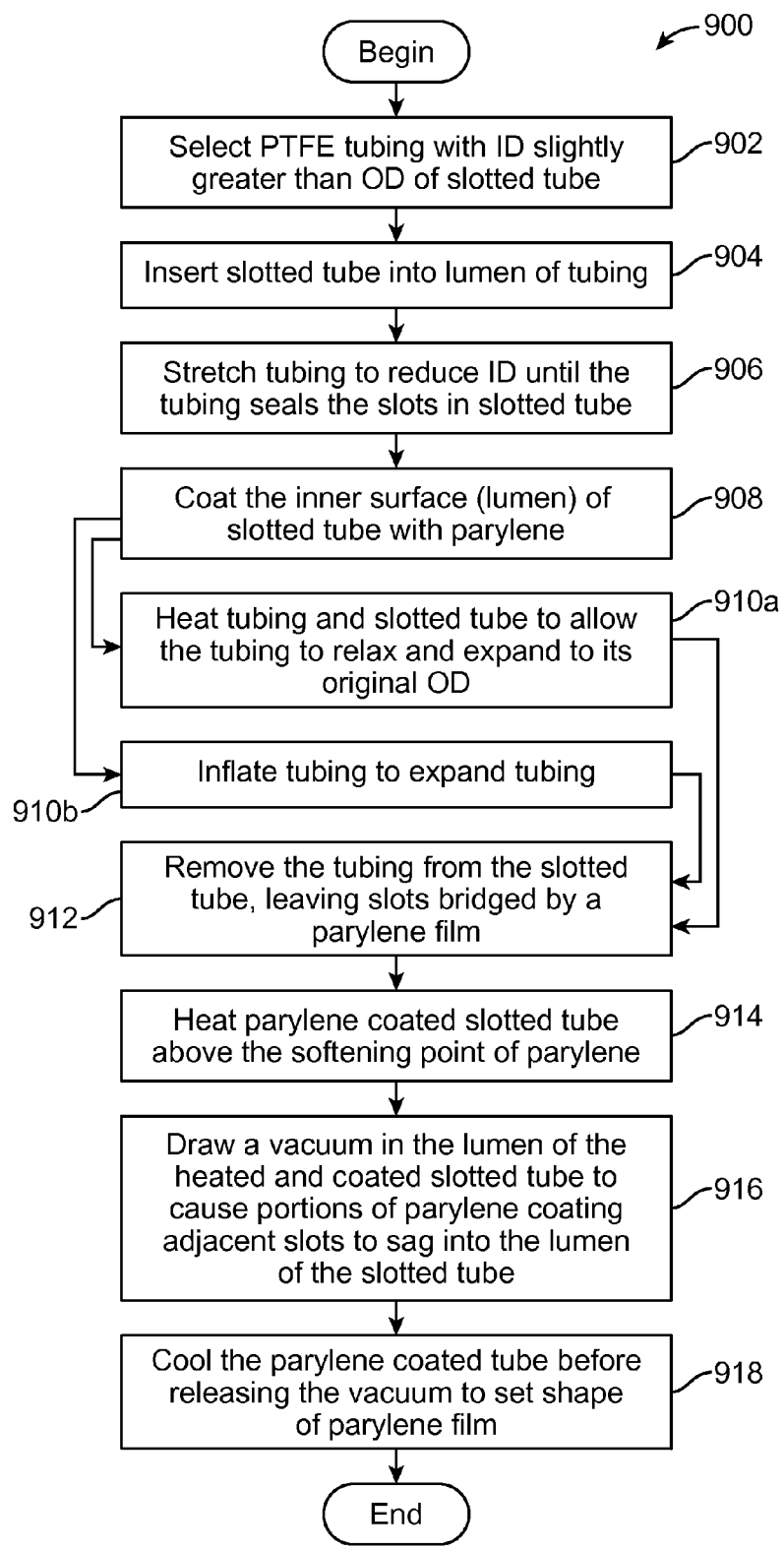

FIG. 23 depicts still yet another method 900 for adding a polymer coating/layer 40 to a slotted tube 26, according to the disclosed inventions. The method 900 is very similar to the method 800 depicted in FIG. 22. The difference between the two methods is that the softened polymer (parylene) coating 40 is drawn inward (step 916) with a vacuum instead of pushed outward with pressure (816). At step 902, a polymer tubing (e.g., a PTFE or similar polymer tubing), with an inner diameter slightly larger than the outer diameter of the slotted tube 26, is selected. At step 904, the slotted tube 26 is inserted into the lumen of the polymer tubing. At step 906, the polymer tubing is stretched to reduce its inner diameter until the tubing seals the slots 28 in the slotted tube 26. At step 908, the inner surface (i.e., the lumen) of the slotted tube 26 is coated with a polymer (e.g., by parylene deposition).

Next, the polymer tubing is expanded for removal from the slotted tube 26 in one (or both) of two ways. In step 910a, the polymer tubing and the slotted tube 26 are heated to allow the tubing to relax and expand to its original inner diameter (i.e., slightly larger than the outer diameter of the slotted tube 26). Alternatively or additionally, the polymer tubing can be expanded by inflation, as described in step 910b. At step 912, the polymer tubing is removed from the slotted tube 26, leaving slots 28 bridged and sealed by a polymer coating 40 (i.e., a parylene film) on the inner surface of the slotted tube 26.

At step 914, the tubular member 26 and the polymer coating 40 disposed thereon are heated until the polymer coating 40 reaches a temperature above its softening point (approximately 280° C. for parylene). At step 916, while the polymer coating 40 is heated to a temperature above its softening point, a vacuum is drawn in the lumen 30 of the tubular member 26 (with the polymer coating 40 on its inner surface). The vacuum pulls the portions (slot-underlying invaginations 46) of the polymer coating into the lumen 30 of the slotted tube 26 below the slots 28.

At step 916, the tubular member 26 and the polymer coating 40 are cooled to below the softening point of the polymer coating 40, while the vacuum is maintained, in order to set the shape of the polymer coating 40. This set shape includes slot-underlying invaginations 46 that invert into the lumen 30 of the tubular member 26 below the slots 28, as shown in FIG. 7E. After the shape of the polymer coating 40 is set, the vacuum can be released at the coated tubular member 26 is ready for further processing to form a medical device.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense.

What is claimed is:

1. A method of manufacturing an elongate flexible medical device, comprising:
    forming a plurality of openings in a wall of an elongate tubular support member to thereby increase a flexibility of the support member;
    forming a layer of sealing material on an outer surface of the support member so as to create a sealed portion of the support member including the plurality of wall openings; and
    forming a plurality of flexible invaginations in the layer of sealing material that overlay respective wall openings in the support member;
    wherein the layer of sealing material is formed by inserting a substrate into an axial lumen of the support member so that the substrate underlies and thereby blocks the respective wall openings, applying a coating of sealing material to the outer surface of the support member, and removing the substrate from the support member lumen; and
    wherein the substrate comprises a polymer beading having an outside diameter slightly greater than a diameter of the support member lumen, the method further comprising
    stretching the polymer beading to thereby neck down its outer diameter to a diameter slightly smaller than a diameter of the support member lumen, wherein inserting a substrate into the support member lumen comprises inserting the stretched polymer beading into the support member lumen;
    heating the polymer beading so that its outer diameter expands to approximately its pre-stretched diameter, thereby creating a tight fit of the polymer beading within the support member lumen, wherein the coating of sealing material is applied to the outer surface of the support member after expanding the outer diameter of the polymer beading so that sealing material is deposited directly on exposed portions of the polymer beading through the wall openings in the support member; and
    stretching and removing the polymer beading from the support member lumen, such that the sealing material remains intact and covers the wall openings in the support member.

2. The method of claim 1, wherein the invaginations are formed in the sealing material by pressurizing the support member lumen relative to atmosphere exterior of the support member after removing the polymer beading therefrom to thereby radially expand portions of the sealing material overlaying the respective wall openings.

3. The method of claim 1, wherein the invaginations are formed in the sealing material by drawing a vacuum within the support member lumen relative to atmosphere exterior of the support member, after removing the polymer beading therefrom, to thereby draw respective portions of the sealing material radially inward through the respective wall openings.

4. The method of claim 1, wherein the polymer beading comprises PTFE.

5. A method of manufacturing an elongate flexible medical device, comprising:
    forming a plurality of openings in a wall of an elongate tubular support member to thereby increase a flexibility of the support member;
    forming a layer of sealing material on an outer surface of the support member so as to create a sealed portion of the support member including the plurality of wall openings; and
    forming a plurality of flexible invaginations in the layer of sealing material that overlay respective wall openings in the support member;
    wherein the layer of sealing material is formed by inserting a substrate into an axial lumen of the support member so that the substrate underlies and thereby blocks the respective wall openings, applying a coating of sealing material to the outer surface of the support member, and removing the substrate from the support member lumen; and
    wherein the substrate comprises a polymer tubing, and wherein the invaginations are formed in the sealing material by pressurizing an inner lumen of the polymer tubing relative to atmosphere exterior of the support member after insertion into the support member lumen to cause portions of the polymer tubing to extend radially outward through respective wall openings in the support member, thereby forming bulges in portions of the sealing material overlaying the wall openings.

6. The method of claim 5, wherein the inner lumen of the polymer tubing is pressurized prior to applying the coating of sealing material to the outer surface of the support member.

7. The method of claim 5, wherein the inner lumen of the polymer tubing is pressurized after applying the coating of sealing material to the outer surface of the support member.

8. The method of claim 5, wherein the polymer tubing comprises PTFE.

* * * * *